(12) United States Patent
Wang et al.

(10) Patent No.: US 8,211,038 B2
(45) Date of Patent: Jul. 3, 2012

(54) MULTIPLE-BIOSENSOR ARTICLE

(75) Inventors: Yi Wang, San Ramon, CA (US); Jared Lee Watkin, Cheltenham (GB); Chad Harold Mace, Hudson, NH (US); Michael Robert Zocchi, Somerville, MA (US); Shridhara Alva Karinka, Pleasanton, CA (US); Mark E. Tess, Merrimack, NH (US)

(73) Assignee: Abbott Diabetes Care Inc., Alameda, CA (US)

( * ) Notice: Subject to any disclaimer, the term of this patent is extended or adjusted under 35 U.S.C. 154(b) by 887 days.

(21) Appl. No.: 10/944,302

(22) Filed: Sep. 17, 2004

(65) Prior Publication Data

US 2006/0064035 A1    Mar. 23, 2006

(51) Int. Cl.
*B65D 81/00* (2006.01)
(52) U.S. Cl. ............. 600/584; 435/4; 204/406; 204/407
(58) Field of Classification Search .......... 600/573–583; 435/4, 817; 204/403, 403.03, 409, 416, 418, 204/419
See application file for complete search history.

(56) References Cited

U.S. PATENT DOCUMENTS

| | | | |
|---|---|---|---|
| 4,635,488 A * | 1/1987 | Kremer ................... 73/864.72 |
| 4,794,926 A * | 1/1989 | Munsch et al. ............... 606/183 |
| 4,865,698 A * | 9/1989 | Terashima ................. 205/779 |
| 5,228,972 A | 7/1993 | Osaka et al. |
| 5,395,504 A | 3/1995 | Saurer et al. |
| 5,407,554 A * | 4/1995 | Saurer .................... 204/403.03 |
| 5,738,244 A | 4/1998 | Charlton et al. |
| 5,741,634 A | 4/1998 | Nozoe et al. |
| 5,854,074 A * | 12/1998 | Charlton et al. ................ 436/46 |
| 6,063,039 A | 5/2000 | Cunningham et al. |
| 6,093,156 A | 7/2000 | Cunningham et al. |
| 6,194,224 B1 * | 2/2001 | Good et al. ................... 436/518 |
| 6,228,100 B1 * | 5/2001 | Schraga ........................ 606/183 |
| 6,428,664 B1 * | 8/2002 | Bhullar et al. ............ 204/403.03 |
| 6,530,892 B1 * | 3/2003 | Kelly ............................. 600/583 |
| 6,706,159 B2 * | 3/2004 | Moerman et al. ......... 204/403.03 |
| 6,939,312 B2 * | 9/2005 | Hodges et al. ................ 600/583 |
| 7,060,192 B2 * | 6/2006 | Yuzhakov et al. .............. 216/11 |
| 7,150,755 B2 * | 12/2006 | Levaughn et al. ............ 606/181 |
| 7,225,008 B1 * | 5/2007 | Ward et al. .................... 600/345 |
| 2003/0054376 A1 * | 3/2003 | Mullis et al. ..................... 435/6 |
| 2003/0083685 A1 * | 5/2003 | Freeman et al. .............. 606/181 |
| 2003/0199894 A1 | 10/2003 | Boecker et al. |
| 2003/0199907 A1 * | 10/2003 | Boecker et al. ............... 606/181 |
| 2005/0149089 A1 * | 7/2005 | Trissel et al. .................. 606/181 |

FOREIGN PATENT DOCUMENTS

| EP | 0 826 963 | 3/1998 |
| WO | 02/100274 | 12/2002 |

OTHER PUBLICATIONS

Bayer Corporation, Glucometer® DEX™ Blood Glucose Monitoring System, User Guide, Jul. 1997, Elkhart, IN, USA.
Roche Diagnostic GmbH, ACCU-CHEK® Compact Blood Glucose Monitor, User's Manual, Nov. 2000, Mannheim, Germany.

* cited by examiner

*Primary Examiner* — Rene Towa
(74) *Attorney, Agent, or Firm* — Edward J. Baba; Marcus T. Hunt; Bozicevic, Field & Francis LLP

(57) ABSTRACT

An article suitable for conducting one or more assays with an apparatus, e.g., a meter, for determining the presence or concentration of an analyte in a sample of biological fluid. The article contains a plurality of biosensors arranged in such a manner that each of the biosensors can be utilized before the article must be removed from the apparatus.

21 Claims, 14 Drawing Sheets

MULTIPLE-BIOSENSOR ARTICLE

BACKGROUND OF THE INVENTION

1. Field of the Invention

This invention relates to biosensors, and in particular, articles containing a plurality of biosensors suitable for use with an apparatus, e.g., an analyte meter, for determining the presence or concentration of analytes in a biological sample.

2. Discussion of the Art

The prevalence of diabetes has been increasing markedly in the world. At this time, diagnosed diabetics represent about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. The individual then coats a paper strip carrying chemistry with the blood, and finally inserts the blood-coated strip into a blood glucose meter for measurement of glucose concentration by determination of change in reflectance.

The medical apparatus of the prior art for monitoring the level of glucose in the blood stream required that an individual have separately available a needle or lancet for collecting blood from the individual, strips carrying blood chemistry for creating a chemical reaction with respect to the glucose in the blood stream and changing color, and a blood glucose meter for reading the change in color indicating the level of glucose in the blood stream. The level of blood glucose, when measured by a glucose meter, is read from a strip carrying the blood chemistry through the well-known process of reading reflectometers for glucose oxidation.

The prior art discloses numerous electrochemical and optical biosensors, e.g., test strips, for measuring the concentration of an analyte in a test sample. In particular, the art discloses disposable test strips for the measurement of glucose level in whole blood that deal primarily with the reaction layer used to generate an analytical response, the mode of measurement, and the algorithms used in the measurement.

Electrochemical assays for determining the concentrations of enzymes or their substrates in complex mixtures of liquids have been developed. Test strips (i.e., biosensors in the form of test strips) are useful in external testing. In external testing, test strips can function in a non-invasive manner (i.e., as strips that come into contact with blood withdrawn by a syringe or a lancing device). In particular, test strips for biomedical applications (e.g., whole blood analyses) have been developed for the determination of glucose levels in biological samples. In general, test strips comprise electrochemical cells in which there can be working electrodes, counter electrodes, and reference electrodes. The potential of the working electrode is maintained at a constant value relative to that of the reference electrode.

A minimally painful technique for obtaining body fluids is described in U.S. Pat. No. 6,063,039. This patent discloses an apparatus for obtaining blood for diagnostic tests. The apparatus comprises a housing having a sealable chamber located therein and a sealable opening in fluid communication with the sealable chamber, a power source, a vacuum pump operably connected to the power source, the vacuum pump in communication with the sealable chamber, a lancing assembly positioned within the sealable chamber, and a fluid collector (biosensor in the form of a test strip) positioned in the sealable chamber, the fluid collector in fluid communication with the sealable opening. However, only one fluid collector can be positioned in the housing of the apparatus at a time. The user must manually remove a consumed fluid collector from the housing, before another fluid collector can be inserted therein. It would be desirable to improve that system in order to allow more than one fluid collector to be inserted into the housing at a time, in order to simplify the use of the apparatus for the user.

Osaka et al., U.S. Pat. No. 5,228,972, discloses an apparatus for measuring concentration of test substances in liquid. The apparatus comprises one or more thin plates having one or more openings through which a test substance to be measured is penetrated, in a predetermined position thereof, diffusion-limiting membranes for limiting diffusion of the test substance adhered to the thin plates for covering the openings, a casing for housing the one or more thin plates, and a driving mechanism for moving the thin plate by a predetermined distance. The thin plate may be disk-shaped, strip-shaped, or elongated. The elongated thin plate may further be rolled. The casing is provided with the driving mechanism and is positioned in a test apparatus body having a concentration-measuring electrode therein. Multiple measurements of concentration of a test substance are carried out by moving the thin plate by the driving mechanism to position the diffusion-limiting membrane having the test solution deposited thereon to the position available to contact with the concentration measuring electrode, while keeping the casing placed in the test apparatus body. However, U.S. Pat. No. 5,228,972 requires a casing and a diffusion-limiting membrane. Moreover, the thin plate must be moved by the driving mechanism to position the diffusion-limiting membrane having the test solution deposited thereon to a position available to contact the concentration-measuring electrode, while keeping the casing placed in the test apparatus body.

Nozoe et al., U.S. Pat. No. 5,741,634, discloses a disk-shaped sensor body containing a plurality of elemental sensors radially extended outward from the circumference thereof. The sensor body is made from an insulating material. The circumferential portion of the sensor body is shaped to have v-shaped notches equidistantly and angularly arrayed therearound. Of these notches, the adjacent notches define a trapezoidal part. The notches and trapezoidal parts are alternately arrayed on the circumference of the sensor body. The sensor elements are formed in the trapezoidal parts. In the sensor circuit, a sensor portion is formed of a counter electrode, a reference electrode, a first working electrode, and a second working electrode. Additional films are positioned over the two working electrodes. However, U.S. Pat. No. 5,741,634 does not provide a means for integrating the measurement function with the sample extraction function and sample transfer function.

The foregoing patents describe several ways to package a plurality of test strips for determining the concentration of analytes. However, neither of these patents disclose a device wherein a device for collection of biological samples and storage of a plurality of biosensors are integrated into a single entity. "Ascensia Breeze" test strips (Bayer) and "Accu-Chek Compact" test strips (Roche) involve packaging a plurality of individual test strips in sealed chambers and indexing unused test strips into position for measuring the concentration of glucose. However, these test strips require complicated advancing and indexing mechanisms to pierce sealed chambers, to advance and index the test strips into position for testing, and to eject used test strips after testing.

SUMMARY OF THE INVENTION

This invention provides an article suitable for conducting one or more assays with an apparatus, e.g., a meter, for determining the presence or concentration of an analyte in a sample of biological fluid. The article contains a plurality of biosensors arranged in such a manner that each of the biosensors can be utilized before the article must be removed from the apparatus.

In one embodiment, the article comprises a thin, flat plate, preferably in the shape of a disk. The thin, flat plate has a plurality of sectors. Each of the sectors has a biosensor applied thereto. Attached to the thin, flat plate is a backing, preferably having substantially the same peripheral dimensions as does the plate. The backing also has a plurality of sectors. The backing can be constructed to facilitate the use of a device for forming an opening in the skin of a subject. In this embodiment, each of the sectors of the backing has a recessed portion for allowing a lancing device to pass therethrough. Each sector in the thin, flat plate has an aperture and each recessed portion in each sector in the backing has an aperture, each of the apertures in the thin, flat plate being in register with an aperture in one of the recessed portions in the backing.

The multiple-biosensor article can be loaded into an analyte meter by inserting the article into a slot located on or in the analyte meter or by opening a door or cover on or in the analyte meter and inserting the article into the area provided. Once loaded in the analyte meter, the multiple-biosensor article can be advanced or indexed or both by either rotating or translating the article automatically, semi-automatically, or manually. Advancing or indexing or both can be carried out by such mechanisms as motor(s), gear(s), pulley(s), belt(s), solenoid(s), nano-muscle(s), and the like. A lancing blade can pass through the apertures in the plate and the backing on the way to lancing the skin.

After the lancing step, the multiple-biosensor article can be indexed slightly to cover the lancing site with the sample pick-up area of a biosensor to fill the reaction site of the biosensor. After a test is completed, the article may be advanced or indexed by rotation, automatically, semi-automatically, or manually, toward a storage area within the analyte meter.

In a second embodiment, the thin, flat plate can be deleted, and the backing can be constructed so as to perform the functions of both the backing and the thin, flat plate of the first embodiment.

In a third embodiment, the biosensors can be manufactured and stored in the form of a roll. The roll comprises a plurality of segments arranged linearly. Each segment contains a biosensor. At least a portion of each segment has an opening therein to allow a lancing device to penetrate the skin without striking the solid portions of the segment. In this embodiment, the segments can be separated by score lines to enable removal and disposal of a used biosensor.

In a fourth and a fifth embodiment, both of which can be in the form of a roll, each segment is attached to an adjacent segment by a hinge. In the fourth embodiment, the hinge is formed of a flexible, tearable material, which can be torn by the hand to detach a given biosensor from the adjacent biosensor. In the fifth embodiment the hinge comprises a pin and a holder for the pin, whereby a given biosensor can be detached from the adjacent biosensor by separating the pin from the holder.

In a sixth embodiment, a single-use lancet can be provided for each biosensor. This embodiment eliminates the need to provide a lancing device having complex cocking and triggering mechanisms.

The invention provides an integrated system comprising an analyte meter and biosensors, wherein the measurement of the concentration of the analyte need not require the intervention of the user for loading biosensors into the analyte meter until the all the biosensors on the article, e.g., the disk or roll, whichever the case may be, are consumed. In those embodiments where a lancet is provided for each biosensor, the user can perform a multiplicity of tests before manual insertion of lancets is required. In those embodiments where sample extraction and retention of used biosensors in the analyte meter are integrated, contamination by biohazards can be reduced.

DETAILED DESCRIPTION

Figure 1:
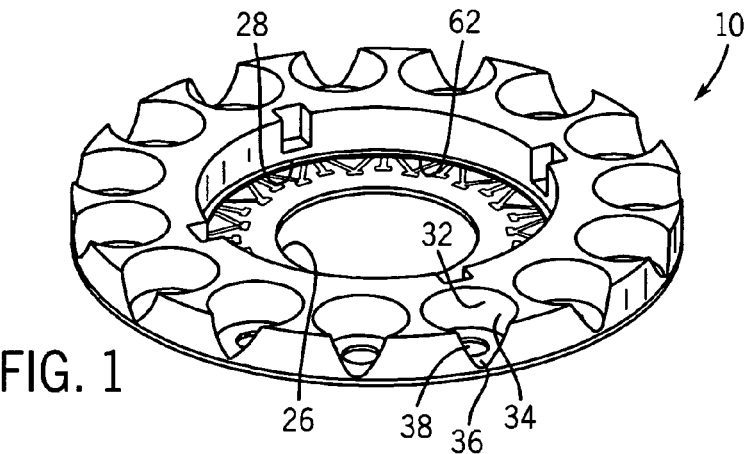
FIG. 1 is a perspective view of one embodiment of the article of this invention.

As used herein, the term "biosensor" means an element of the article of this invention that provides qualitative or quantitative information relating to an analyte in a biological sample. A biosensor contains a biological component such as enzyme, antibody, etc., to impart selectivity to the analyte of interest in a complex sample, such as biological fluid, e.g., blood, interstitial fluid.

As used herein, the expression "test strip" means a biosensor in the form of a strip that contains the necessary components to generate a measurable signal when exposed to a liquid sample. Test strips are typically single-use, disposable articles. In general, a test strip comprises a backing having an electrode arrangement thereon.

As used herein, the term "sector" means a region of the article of the invention that contains a single electrode arrangement and a set of apertures for positioning a biosensor at a sample receiving site and transferring the received sample from the sample receiving site to a reaction site. In certain embodiments of this invention, the article comprises a plurality of sectors arranged such that each sector is adjacent to two neighboring sectors.

As used herein, the term "sector" means a part in which the entirety of the article can be divided. A sector contains a single electrode arrangement and a set of apertures for positioning a biosensor at a sample receiving site and transferring the received sample from the sample receiving site to a reaction site. In certain embodiments of this invention, the article comprises a plurality of sectors arranged such that each sector is adjacent to two neighboring sectors As used herein, the term "segment" also means a part in which the entirety of the article can be divided. A segment contains a single electrode arrangement and a set of apertures for positioning a biosensor at a sample receiving site and transferring the received sample from the sample receiving site to a reaction site. In certain embodiments of this invention, the article comprises a plurality of segments arranged such that each segment is adjacent to two neighboring segments. In general, the term "sector" is used to describe circular embodiments, and the term "segment" is used to describe linear embodiments.

As used herein, the expression "electrode arrangement" means the manner in which electrodes are arranged to form a biosensor. Typically, the electrode arrangement of a biosensor comprises a working electrode, a reference electrode, and a counter electrode (or in place of the reference electrode and counter electrode an electrode that functions as both reference electrode and counter electrode). Reagents that are required for generating a measurable signal upon electrochemical reaction with an analyte in a sample to be assayed are placed over the electrodes so that the reagents cover at least one of the electrodes. In some cases, the reagents and an inert electrode (such as carbon, palladium, gold) serve as the working electrode and the dual-purpose reference/counter electrode. In these situations, the reagents are required to be on both electrodes.

Figure 3:
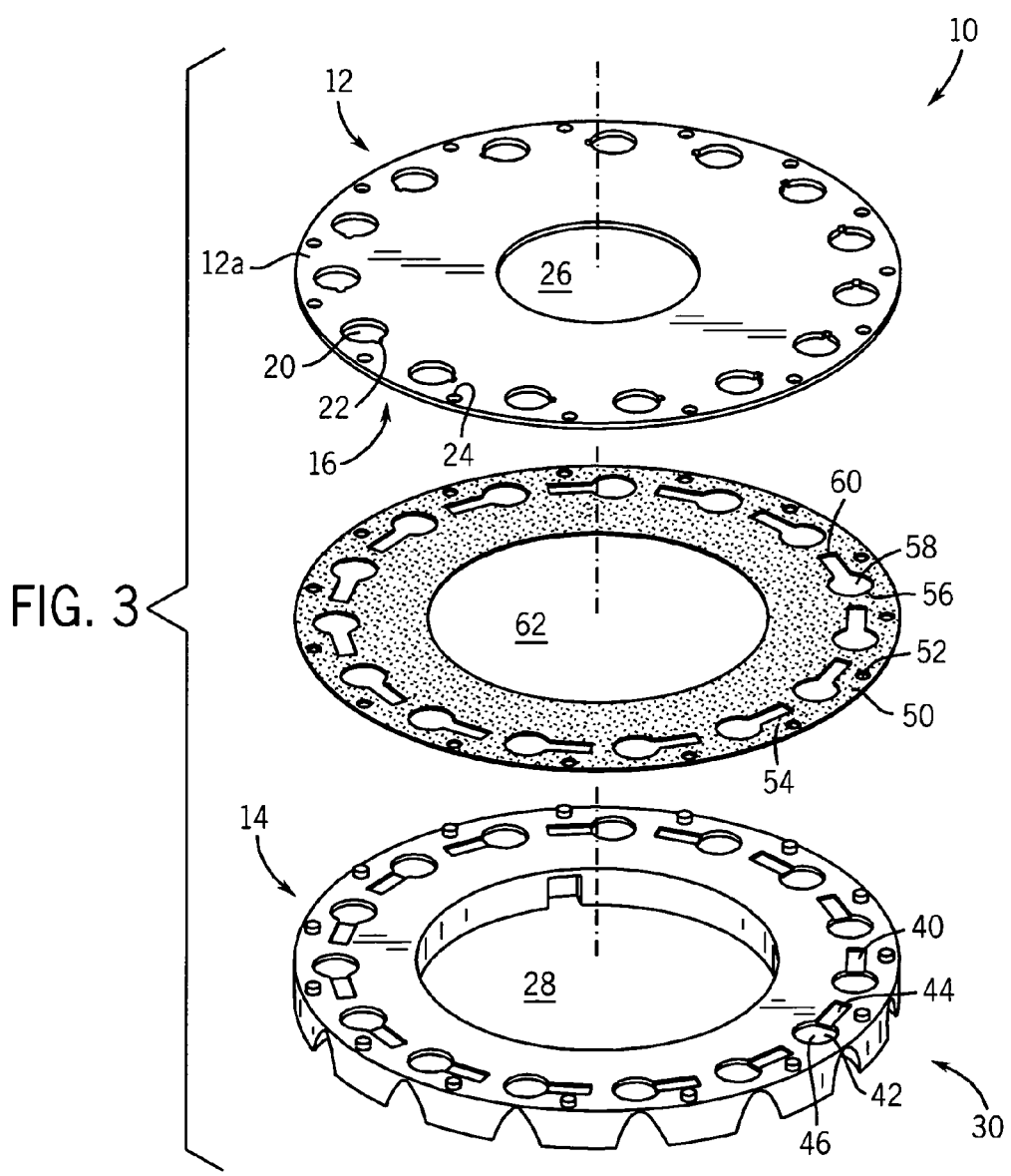
FIG. 3 is an exploded perspective view of the article of FIG. 1, wherein the wherein the plate of the article is shown above the backing of the article. An optional layer of adhesive is shown between the plate and the backing.
Figure 2:
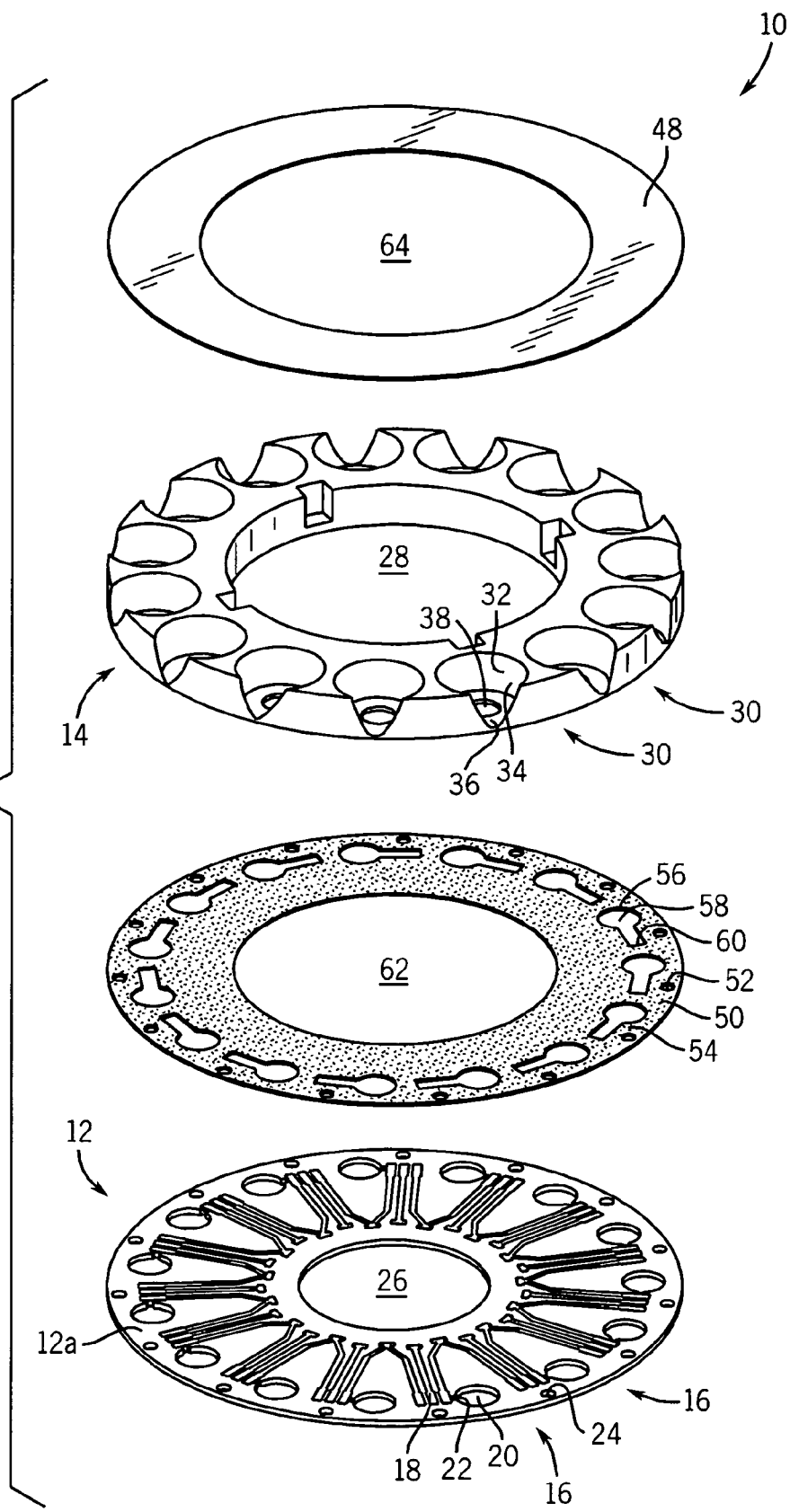
FIG. 2 is an exploded perspective view of the article of FIG. 1, wherein the backing of the article is shown above the plate of the article, and an optional shield is shown above the backing. An optional layer of adhesive is shown between the plate and the backing.

Referring now to FIGS. 1-3, which illustrate one embodiment of this invention, the article 10 comprises a thin, flat plate 12 and a backing 14. The thin, flat plate 12 is in the form of a disk and has a plurality of sectors 16, each of which contains a biosensor 18 on a major surface 12a thereof. Each biosensor 18 comprises an electrode arrangement, which will be described later. The thin, flat plate 12 further comprises a plurality of apertures 20, each aperture 20 being adjacent to an electrode arrangement of a given biosensor 18. Each of the apertures 20 is shown as being circular in shape, although other shapes, e.g., elliptical, triangular, rectangular, are suitable for the invention. The purpose of the aperture 20 is to provide an opening through which a lancing element may pass in order to form an opening in the skin of a subject or patient. Each aperture 20 further has a notch 22 formed at the boundary thereof. The purpose of the notch 22 is to provide an area at which a biological sample from the subject or patient can easily be drawn into the biosensor 18. The notch 22 breaks the surface tension of the liquid and provides a larger surface area for application of a liquid sample.

The thin, flat plate 12 may further comprise a plurality of relatively small apertures 24, each relatively small aperture 24 being adjacent to a given electrode arrangement. The purpose of the small apertures 24 is to receive a pin or other type of fastener to properly align the backing 14 with the thin, flat plate 12. In the embodiment shown in FIGS. 1-3, the thin, flat plate 12 has a relatively large aperture 26 in the center thereof. The purpose of the relatively large aperture 26 is to allow a drive assembly to be positioned to engage the article 10 of this invention.

The backing 14 is substantially congruent with the thin, flat plate 12. The backing 14 has a thickness greater than the thickness of the thin, flat plate 12. In the embodiment shown in FIG. 1, the backing 14 has a relatively large aperture 28 in the center thereof. The purpose of the relatively large aperture 28 is to allow a drive assembly to be positioned to engage the article 10 of this invention.

In addition, the backing 14 has a plurality of sectors 30, each sector 30 corresponding to a sector 16 of the thin, flat plate 12. Each sector 30 has a recessed portion 32 having a wall portion 34 and a base portion 36, the base portion 36 preferably being circular in shape. In the base portion 36 of each sector 30 is an aperture 38. When the thin, flat plate 12 and the backing 14 are properly assembled, each aperture 38 is in register with an aperture 20 of the thin, flat plate 12.

In the embodiment shown in FIGS. 1-3, the backing 14 has fifteen (15) sectors 30, each having a recessed portion 32. The purpose of the recessed portion 32 is to provide a guiding path for a lancing device (not shown) to travel in order to reach the skin of the user of the article of this invention. The area of the recessed portion 32 (i.e., the area of the base portion 36) must be sufficiently great to allow passage of the lancing device. The depth of the recessed portion (i.e., the length of the wall portion 34) must be sufficiently great to allow the lancet to be guided to its target but not so great as to obstruct or otherwise hinder the movement of the lancet.

In addition, in the embodiment shown in FIGS. 1-3, there are fifteen (15) apertures 20 in the thin, flat plate 12 and fifteen (15) apertures 38 in the backing 14, each sector 30 in the backing 14 having one aperture 38 and each sector 16 in the thin, flat plate 12 having one aperture 20. The apertures 38 in the backing 14 and the apertures 20 in the thin, flat plate 12 are aligned, whereby a lancing device passes through both apertures 20 and 38 to form an opening in the skin, and biological fluid, typically blood, begins its flow to a biosensor 18 from the aperture 20. The particular size of the apertures 20 and 38 is not critical, but if they are too large, the number of biosensors 18 that can be disposed on a thin, flat plate 12 will be reduced, and if they are too small the rate of flow of biological fluid will be too low. The size of the apertures 20 and 38 can be selected to (a) optimize the number of biosensors 18 that can be retained on the thin, flat plate 12 and (b) the rate of flow of the biological fluid.

In the embodiment shown in FIGS. 1-3, the major surfaces of the thin, flat plate 12 are circular in shape to facilitate advancement of the biosensors 18 in an apparatus, i.e., meter, i.e., an analyte meter. While possibly not as effective as a circular shape, other shapes, e.g., elliptical, triangular, rectangular, can be employed. The dimensions of the thin, flat plate 12 are not critical. However, it is desired that the thin, flat plate 12 at least have sufficient surface area to carry a single day's supply of biosensors 18, typically three to four biosensors 18. As biosensors 18 are reduced in size, it is expected that as many as twenty-five to thirty-five biosensors 18 can be carried on the thin, flat plate 12. The thickness of the thin, flat plate 12 is not critical, but it should be sufficiently thick to ensure structural integrity. Typical dimensions of the thin, flat plate 12 can range from about 1 cm to about 10 cm in diameter and from about 0.5 mm to about 5 mm in thickness.

Because the thin, flat plate is expected to be disposable, it is preferred that the thin, flat plate 12 be constructed of a relatively inexpensive material, such as, for example, sheet metal, rigid, semi-rigid, or flexible polymeric materials, paper, e.g., card stock. Examples of materials suitable for use in making the thin, flat plate 12 include, but are not limited to, polyvinyl chloride, polyester, polycarbonate, and polyethylene terephthalate.

The backing 14 can be cylindrical in shape to facilitate advancement of the biosensors 18 in the apparatus, i.e., an analyte meter. The surface of the backing 14 is preferably of a shape that is substantially similar to that of the thin, flat plate 12, that is, if the major surfaces of the thin, flat plate 12, for example, are elliptical, triangular, or rectangular, it is preferred that the major surfaces of the backing 14 also be elliptical, triangular, or rectangular, respectively. The area of the surface of the backing 14 is preferably substantially equal to that of the thin flat plate 12. The overall depth of the backing 14 is not critical, but should be of sufficient length to ensure structural integrity. The depth must not be so great as to require the apparatus into which it is inserted to be excessively large. Typical dimensions of the backing 14 can range from about 1 cm to about 10 cm in diameter and from about 0.5 to about 5 mm in thickness. The backing 14, like the thin, flat plate 12, is preferably made of an inexpensive material, because it too is intended to be disposable. Preferred materials for constructing the backing 14 include polymeric materials, paper, other cellulosic materials. Because the backing 14 includes flat surfaces, recesses, and apertures, it is preferred that it be made of a polymeric material, whereby it can be formed by means of a molding process for forming shaped articles. Examples of materials suitable for use in making the backing 14 include, but are not limited to, polyester, polyethylene terephthalate, and polycarbonate. In general, the backing can be made of any material that can be easily shaped to a three-dimensional component to support the biosensors. Paper and foil can be used, but are not easily shaped into a three-dimensional article having a substantial depth.

The major surface of the backing 14 that faces the thin, flat plate 12 has a plurality of channels 40 formed therein to allow for the flow of a liquid sample. As shown in FIG. 3, one end 42 of the channel 40 is in register with the aperture 20 to enable ease of transfer of biological fluid to the channel 40. The other end 44 of the channel 40 terminates at a vent opening or at the physical end of the channel 40 or, if used, at a flow terminating interface. The portion of the channel 40 between the two ends 42 and 44 can include a surfactant-coated mesh to aid the wicking of the sample into the reaction site. In other embodiments, the dimensions of the channel can be selected to allow the sample to be taken into the reaction site by capillary attraction. The article of this invention has flow channels to direct flow and allow reduction of the volume of sample. Flow channels having the appropriate dimensions could eliminate the use of a layer of mesh. Alternatively, a layer of mesh could be laminated onto the backing, thereby reducing the costly step of applying the mesh to the electrode arrangement.

Each sector 30 of the article 10 has a channel 40. At the end 42 of the channel 40 is a reaction site 46. The volume of the channel 40 is selected to contain the amount of sample needed to perform a test, e.g., an assay to determine the concentration of glucose in blood. The selection of the volume is based on spacing of the electrodes of the electrode arrangement. The dimensions of the channel 40 are derived from the volume of liquid sample required. A typical volume for the channel 40 ranges from about 0.1 microliter to about 4 microliters, thereby calling for dimension of from about 0.5 mm×0.2 mm×0.1 mm to about 2 mm×1 mm×0.2 mm for a rectangularly-shaped channel.

The backing 14 can provide several functions for enhancing the use of a lancing device, such as, for example, a motion-terminating element (not shown) for a mechanical lancing device or a support 48 for a light-generating device, e.g., a laser, to prevent contamination of laser optics. The support 48 can be designated an optical shield. FIG. 2 shows an optical shield 48 for the prevention of contamination of a laser. The optical shield is not required, but may be a desirable option.

A layer of adhesive 50 can be used to adhere the backing 14 to the thin, flat plate 12. The layer of adhesive 50 is preferably placed between the major surface of the thin, flat plate 12 that faces the major surface of the backing 14. The purpose of the layer of adhesive 50 is to maintain the thin, flat plate 12 and the backing 14 in proper registration. The layer of adhesive 50 has small apertures 52 for alignment with the small apertures 24 of the thin, flat plate 12. The layer of adhesive 50 has a plurality of channels 54. One end 56 of each channel 54 has an aperture 58 that is in register with the apertures 20 and 38 in the thin, flat plate 12 and the backing 14, respectively. The other end 60 of the channel is in communication with a vent opening, if necessary. While a layer of adhesive 50 can be used to bond the thin, flat plate 12 to the backing 14, other types of fasteners can be used to bond the thin, flat plate 12 to the backing 14. Alternatives to the use of an adhesive for maintaining the backing and the thin, flat plate in proper registration or alignment include a press-fit ring and the use of alignment posts or pins.

Figure 6:
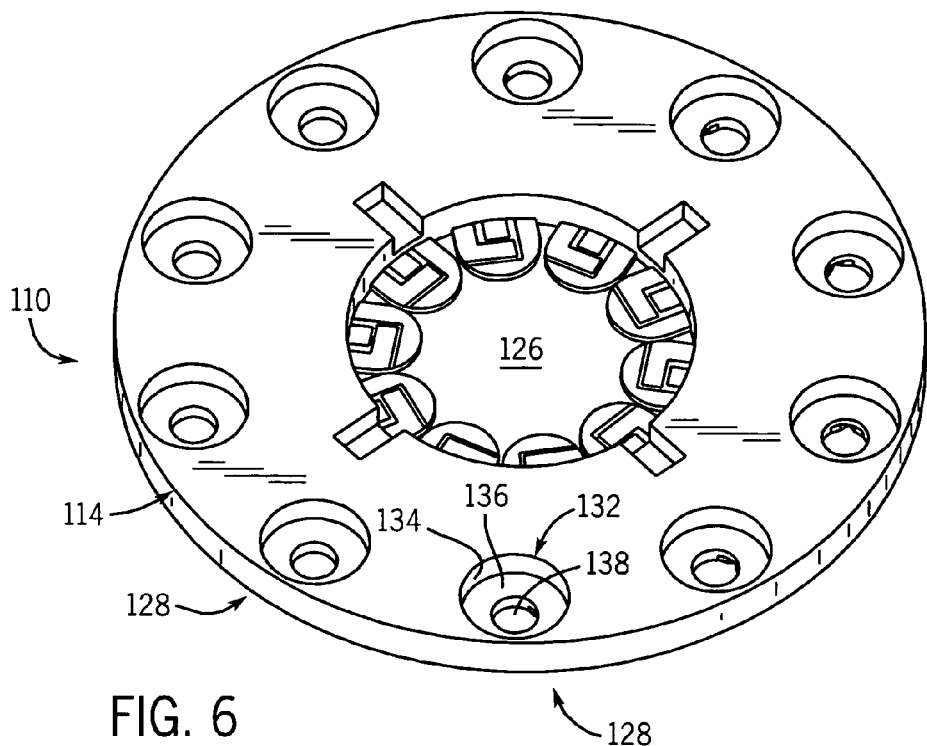
FIG. 6 is a perspective view of another embodiment of the article of this invention.
Figure 7:
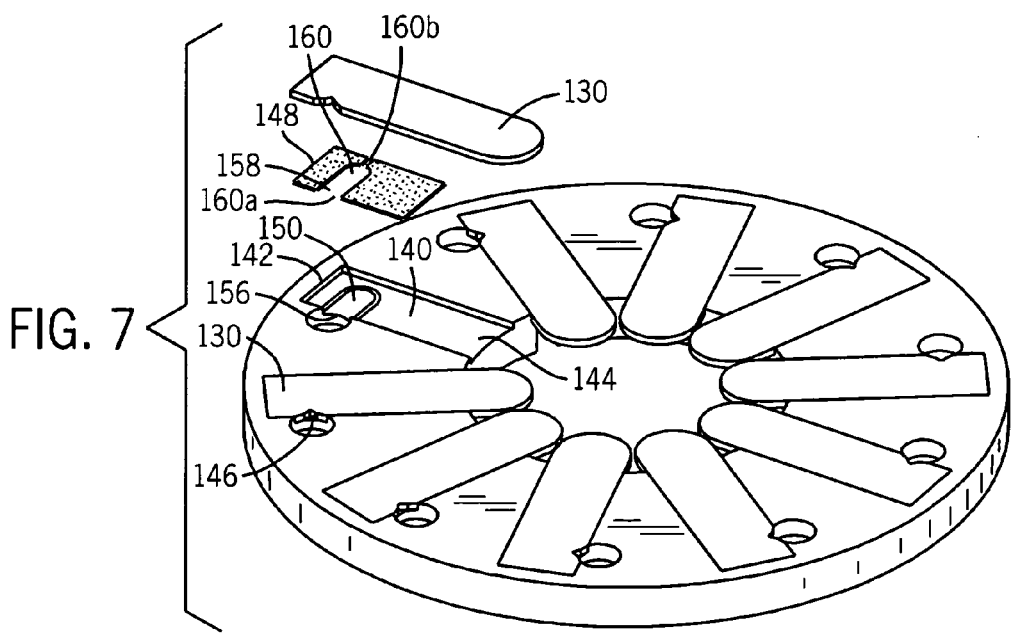
FIG. 7 is an exploded perspective view of the article of FIG. 6, wherein the positioning of the biosensors relative to the recesses is shown.
Figure 8:
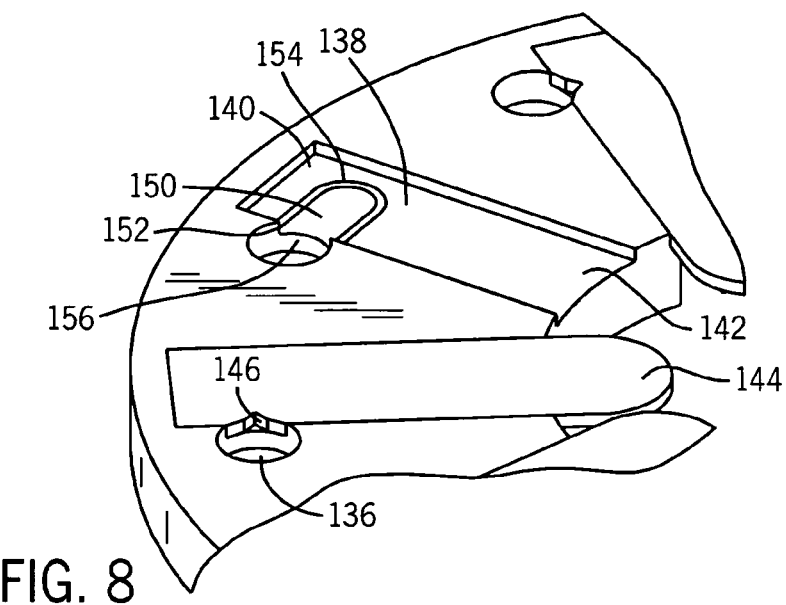
FIG. 8 is a perspective view, greatly enlarged, of the surface of a recess of the article of FIG. 7.

A second embodiment of the article of this invention is shown in FIGS. 6-8. This embodiment does not utilize a thin, flat plate analogous to plate 12. Instead, this embodiment utilizes a backing that receives biosensors that are pre-manufactured test strips, wherein each test strip is received into a recess in the backing. In this embodiment the article 110 comprises a backing 114. The backing 114 is substantially in the form of a cylinder. In the embodiment shown in FIGS. 6-8, the backing 114 has a relatively large aperture 126 in the center thereof. The large aperture 126 performs the same function as do the large apertures 26 and 28 of the first embodiment (see FIGS. 1-3). In addition, the backing 114 has a plurality of sectors 128, each sector 128 capable of retaining a test strip 130. Each sector 128 has a recessed portion 132 having a wall portion 134 and a base portion 136. As shown in FIG. 6, the base portion 136 is circular in shape. In the base portion 136 of each sector 128 is an aperture 138. The purpose and characteristics of the recessed portion 132 are the same as that of the recessed portion 32 of the first embodiment (see FIGS. 1-3).

The major surface of the backing 114 opposite to the major surface of the backing 114 bearing the recessed portions 132 has recesses 140 formed therein to allow for the placement of the test strips 130. As shown in FIGS. 7 and 8, one end 142 of each recess 140 is adjacent to an aperture 138. The other end 144 of each recess 140 terminates at the boundary of the large aperture 126. The portion of the recess 140 between the two ends 142 and 144 has dimensions whereby the recess 140 is capable of accommodating a biosensor in the form of a test strip 130. Each of the apertures 138 is shown as being circular in shape, although other shapes, e.g., elliptical, triangular, rectangular), are suitable for the invention. Each aperture 138 further has a notch 146 formed at the boundary thereof. The purpose of the notch 146 is to provide an area at which the biological sample can easily be drawn into the test strip 130. The notch 146 breaks the surface tension of the liquid and provides a larger surface area for application of a liquid sample. A layer of adhesive 148 can be used to adhere the test strip 130 to the recess 140 in the backing 114.

The backing 114 can be cylindrical in shape to facilitate advancement of the test strips 130 in the meter, i.e., an analyte meter. The major surfaces of the backing 114 can be of any shape that would allow advancement of the test strips 130 in the apparatus. Such shapes include, but are not limited to, circular, elliptical, triangular, or rectangular, respectively. The area of the surface of the backing 114 should be sufficient to accommodate the desired number of test strips. The overall depth of the backing 114 is not critical, but should be of sufficient length to ensure structural integrity. The depth must not be so great as to require the apparatus into which it is inserted to be excessively large. Typical dimensions of the backing 114 can range from about 1 cm to about 10 cm in diameter and from about 0.5 to about 5 mm in thickness.

The backing 114 is preferably made of an inexpensive material, because it is intended to be disposable. Preferred materials for constructing the backing 114 include polymeric materials, paper, other cellulosic materials. Because the backing 114 includes flat surfaces, recesses, and apertures, it is preferred that it be made of a polymeric material, whereby it can be formed by means of a molding process for forming shaped articles. Examples of materials suitable for preparing the backing include, but are not limited to, polyester, polyethylene terephthalate, and polycarbonate.

The major surface of the backing 114 that contains the recessed portions 132 has a plurality of channels 150 formed therein to allow for the flow of a liquid sample. As shown in FIGS. 7 and 8, one end 152 of the channel 150 is adjacent to the aperture 138 to enable transfer of biological fluid from the subject to the channel 150. The other end 154 of the channel 150 terminates at a vent opening or a physical end of the channel or at a flow-terminating interface. The portion of the channel 150 between the two ends 152 and 154 can include a surfactant-coated mesh to aid the wicking of the sample into the reaction site. In other embodiments, the dimensions of the channel can be selected to allow the sample to be taken into the reaction site by capillary attraction.

Each sector 128 has a channel 150. At the end 152 of the channel 150 is a reaction site 156. The volume of the channel 150 is selected to contain the amount of sample needed to perform a test. The selection of the volume is based on the spacing of the electrodes of the electrode arrangement. The dimensions of the channel 150 are derived from the volume of liquid sample required. A typical volume for the channel 150 ranges from about 0.1 microliter to about 4 microliters, thereby calling for dimension of from about 0.5 mm×0.2 mm×0.1 mm to about 2 mm×1 mm×0.2 mm for a rectangularly-shaped channel.

The layer of adhesive 148 has an aperture 158 into which the biological fluid can pass into a channel 160 formed in the layer of adhesive 148. The channel 160 has a first end 160a and a second end 160b.

The backing 114 can provide several functions for enhancing the use of a lancing device, such as, for example, a motion-terminating element (not shown) for a mechanical lancing device or a support for a light-generating device, e.g., a laser, to prevent contamination of laser optics. The support can be designated an optical shield and is substantially similar to the support 48 shown in FIG. 2.

In this embodiment, elimination of the thin, flat plate and the layer of adhesive joining the thin, flat plate to the backing can lead to decreased manufacturing complexity and cost. The backing can also define the perimeter of the channel through which the biological fluid flows, which can lead to tighter tolerances in the perimeter of the channel, hence, tighter tolerances in the volume of the channel.

Figure 11:
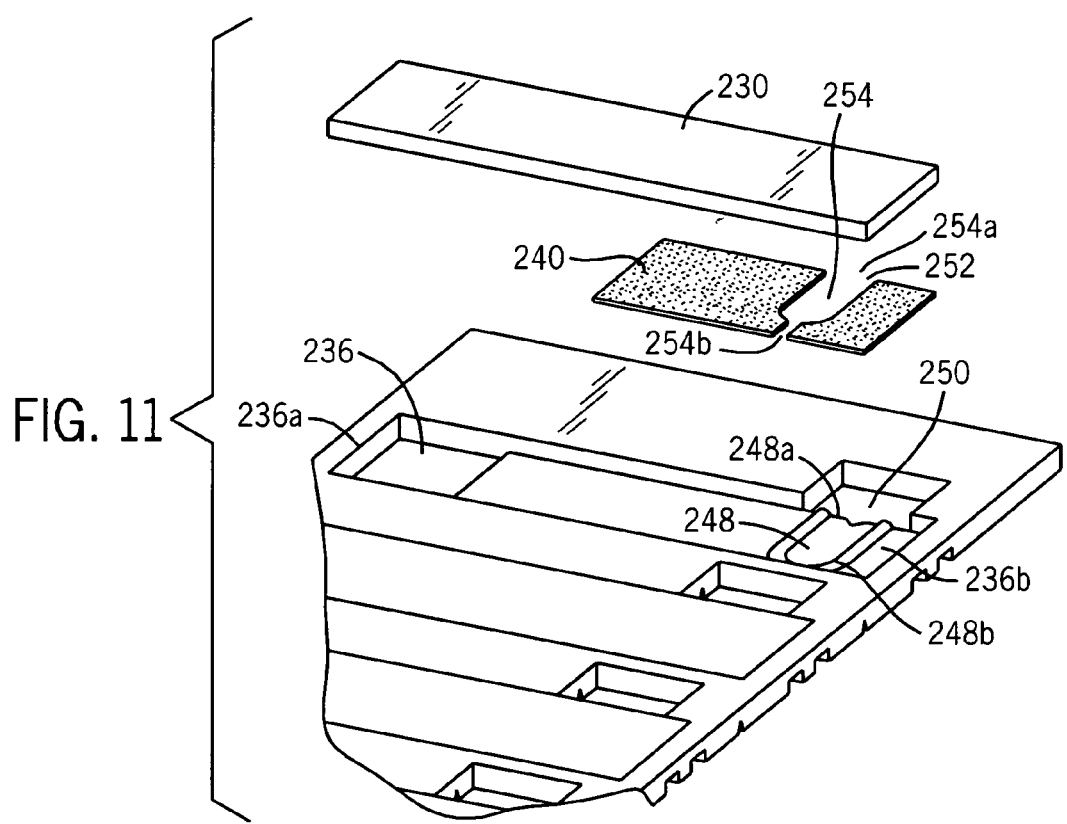
FIG. 11 is an exploded perspective view, greatly enlarged, of the article of FIG. 9, wherein the positioning of the biosensors relative to the recesses is shown. The major surface of the biosensor bearing the electrode arrangement is not shown.
Figure 9:
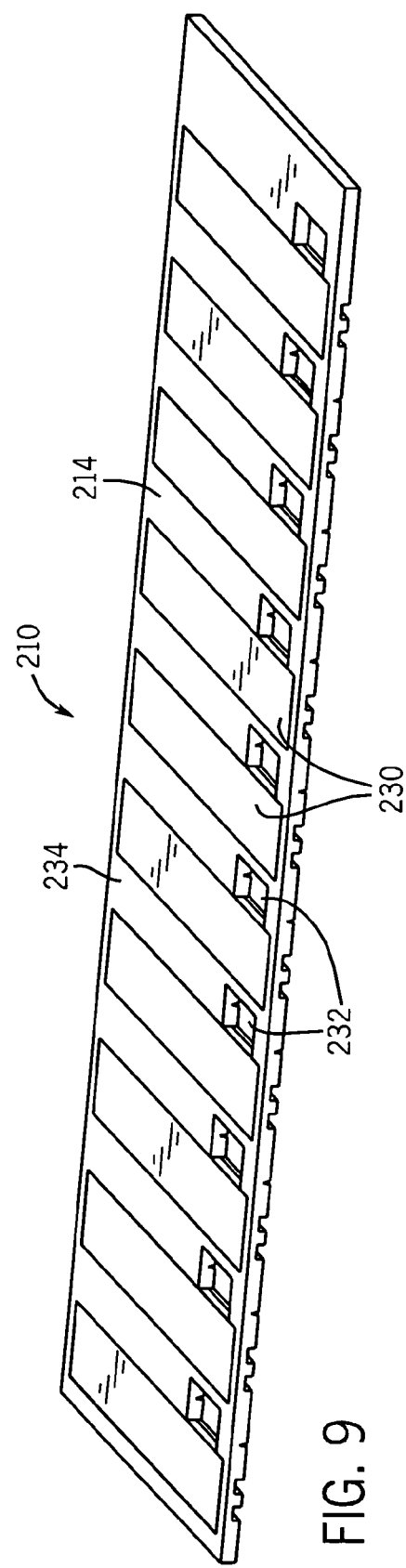
FIG. 9 is a perspective view of another embodiment of the article of this invention. In this figure, the article is shown as being unrolled. Also, in this figure, one major surface of each biosensor in the article is visible.
Figure 10:
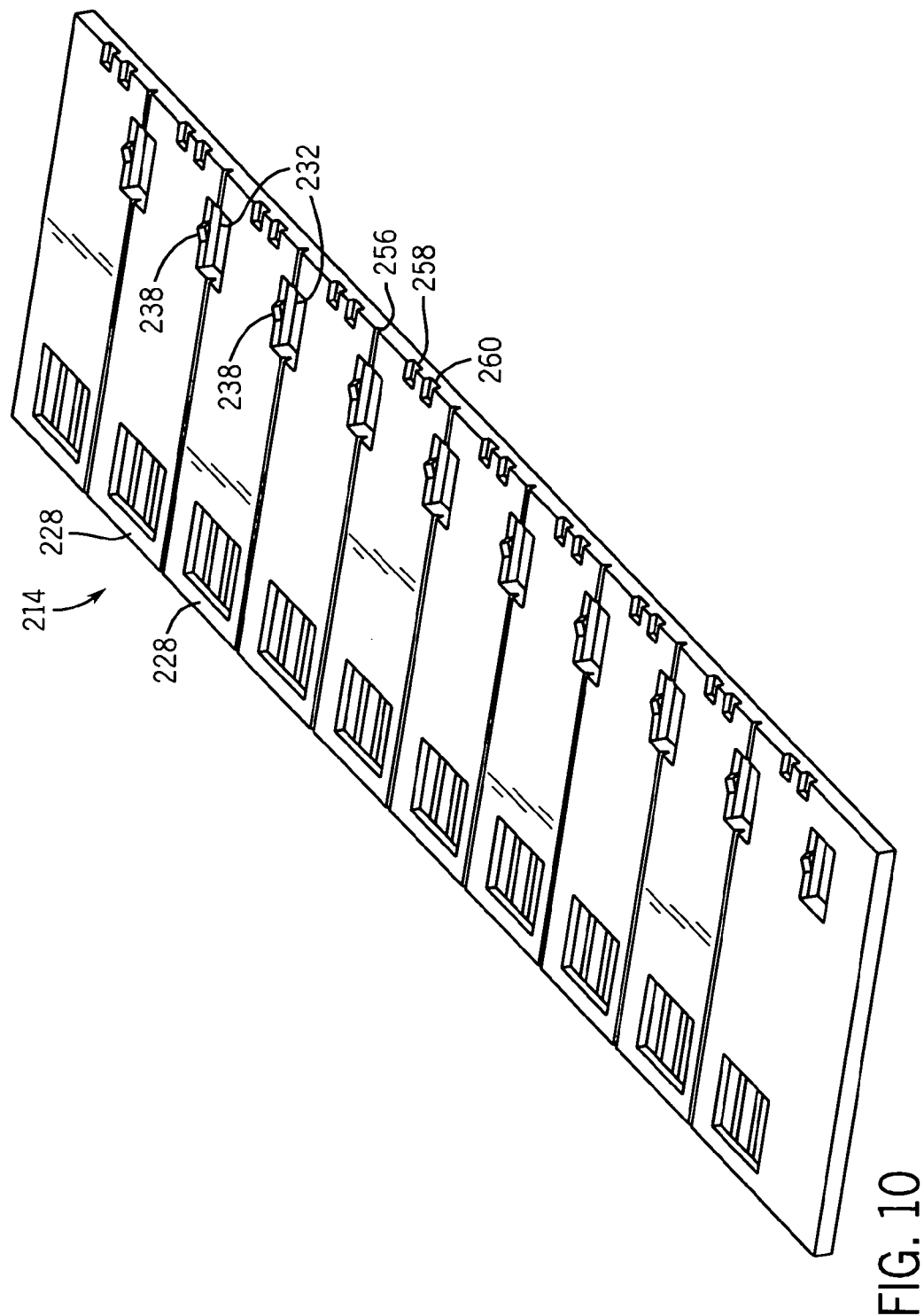
FIG. 10 is a perspective view of the embodiment of the article of FIG. 9. In this figure, the article is shown as being unrolled. Also, in this figure, a major surface of each biosensor in the article, the surface bearing the electrode arrangement, is not visible.

A third embodiment is shown in FIGS. 9-11. In this embodiment, in which the biosensors can be packaged in a configuration that is somewhat similar to a roll or a cartridge, as in a film cartridge, the article 210 comprises a backing 214, which comprises a plurality of segments 228 that are arranged in a line. Other configurations for attaching a plurality of segments include, but are not limited to, the following: (a) a fan-fold configuration, in which the segments resemble the folds of a fan or the pleated bellows of an accordion; (b) a round track configuration, which resembles a roll; (c) an L-shaped configuration, in which the segments do not form a closed loop. Each segment 228 is detachable from the segment 228 or segments 228 adjacent thereto. Each segment 228 has sufficient surface area to support a biosensor 230, e.g., a biosensor in the form of a test strip. In each segment 228, there is an aperture 232 adjacent to the test strip 230. The purpose of the aperture 232 is to allow passage of a lancing device for forming an opening in the skin and further for allowing biological fluid emerging from the opening in the skin to have access to the biosensor 230. On one major surface 234 of the backing 214 are a plurality of recesses 236, one recess 236 per segment 228. These recesses 236 have the function of positioning and retaining the biosensors 230.

The biosensor 230 in each segment 228 has access to the aperture 232 through which biological fluid emerges from the subject or patient. As shown in FIGS. 9-11, the aperture 232 is rectangular in shape and part of the aperture 232 is allocated to a given segment and part of the aperture 232 is allocated to the adjacent segment. However, the aperture 232 can be of a different shape and can be confined within a given segment. The aperture 232 of each segment 228 has a notch 238 for providing an area at which the biological sample can easily be drawn into the test strip 230. As in the embodiments shown in FIGS. 1-3 and 6-8, the notch 238 breaks the surface tension of the liquid and provides a larger surface area for application of a liquid sample. A layer of adhesive 240 can be used to adhere the test strip 230 to the backing 214.

Each of the recesses 236 has a first end 236a and a second end 236b and is of sufficient size and appropriate shape to accommodate a biosensor in the form of a test strip 230. The depth of the recess 236 is approximately equal to or greater than the thickness of the test strip 230. The length of the recess 236 is approximately equal to or greater than the length of the test strip 230. The test strip will be described later.

As stated previously, the article 210 is in the form of a roll or cartridge, as in a film cartridge. The article 210 preferably contains a sufficient number of segments 228 for accommodating the desired number of test strips. The number of segments 228 in the article determines the length of the article. The overall depth of the backing 214 is not critical, but should be of sufficient length to ensure structural integrity. The depth must not be so great as to require the apparatus into which it is inserted to be excessively large. Further, the depth must not be so great that the article cannot be stored in the form of a roll. Typical dimensions of the backing 214 can range and from about 0.5 to about 5 mm in thickness. Each segment 228 should be of sufficient width to accommodate a single test strip 230. The backing 214 can be made of the same type of material that can be used to form the backing 114.

Each segment 228 has a channel 248 formed therein to allow for the flow of a liquid sample. As shown in FIG. 11, one end 248a of the channel 248 is adjacent to the aperture 232 to enable transfer of biological fluid from the subject to the channel 248. The other end 248b of the channel 248 terminates at a vent opening or a physical end 248 between the two ends 248a and 248b can include a surfactant-coated mesh to aid the wicking of the sample into the reaction site. In other embodiments, the dimensions of the channel can be selected to allow the sample to be taken into the reaction site by capillary attraction.

At the end 248a of the channel 248 is a reaction site 250. The volume of the channel 248 is selected to contain the amount of sample needed to perform a test. The selection of the volume is based on the spacing of the electrodes of the electrode arrangement. The dimensions of the channel 248 are derived from the volume of liquid sample required. A typical volume for the channel 248 ranges from about 0.1 microliter to about 4 microliters, thereby calling for dimension of from about 0.5 mm×0.2 mm×0.1 mm to about 2 mm×1 mm×0.2 mm for a rectangularly-shaped channel.

The layer of adhesive 240 has an aperture 252 into which the biological fluid can pass into a channel 254 formed in the layer of adhesive 240. The channel 254 has a first end 254a and a second end 254b.

In one desirable variation of this embodiment, the segments 228 can be rendered more easily detachable from one another by means of perforations or score lines 256 between the segments 228. Adjacent segments can be separated by either tearing along a perforation, or score line, or having a cutting device disconnect a given segment from an adjacent segment. In each segment 228 there can be slot 258 formed therein for facilitating the advancing of the segments 228 for moving the notch 238 closer to the sample of biological fluid emerging from the skin and through the aperture 232 so that the biological fluid can be readily taken up at the sample application site of the test strip 230. A slot 260 adjacent to the slot 258 can be used for indexing of the segments 228 in order to transport a used test strip 230 away from the lancing zone.

Figure 12:
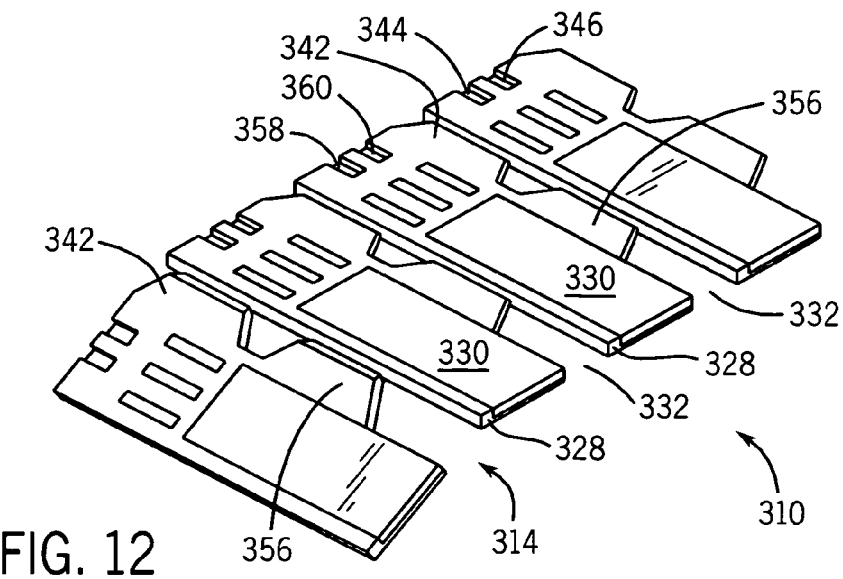
FIG. 12 is a perspective view of another embodiment of the article of this invention. In this figure, the article is shown as being unrolled. Also, in this figure, one major surface of each biosensor in the article is visible.
Figure 13:
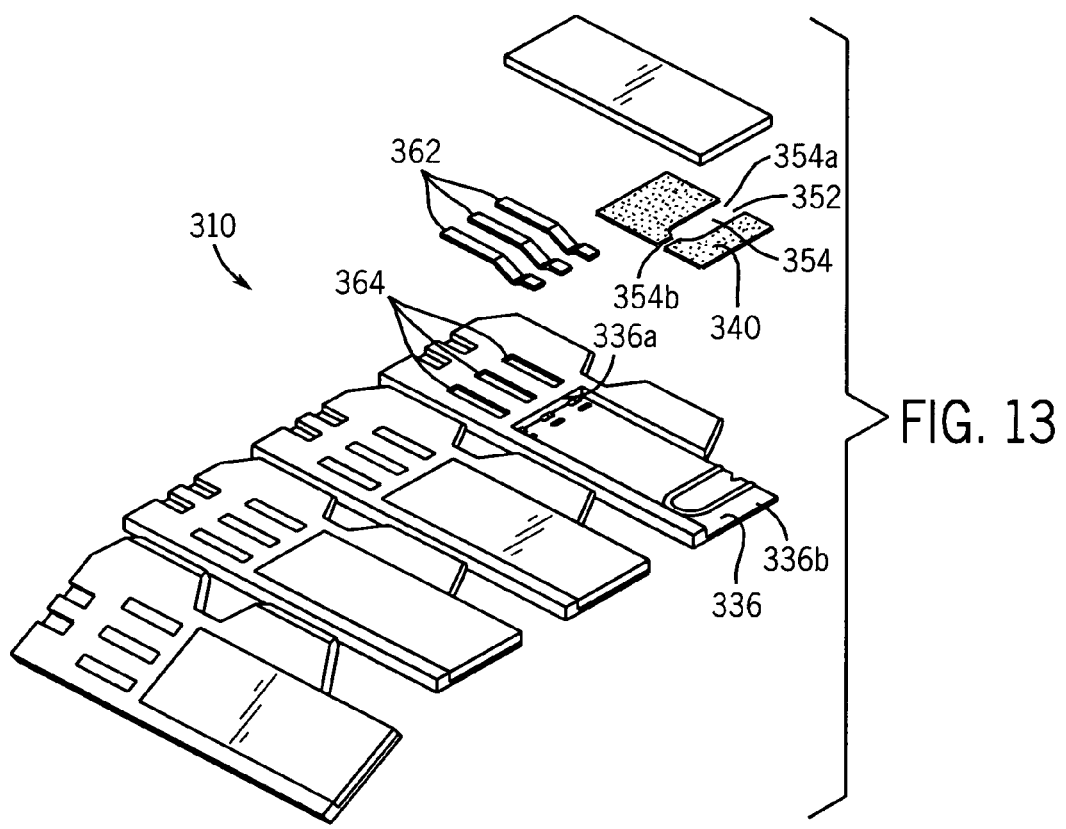
FIG. 13 is an exploded perspective view of the article of FIG. 12. In this figure, the article is shown as being unrolled. Also, in this figure, a major surface of each biosensor in the article, the surface bearing the electrode arrangement, is not visible.
Figure 14:
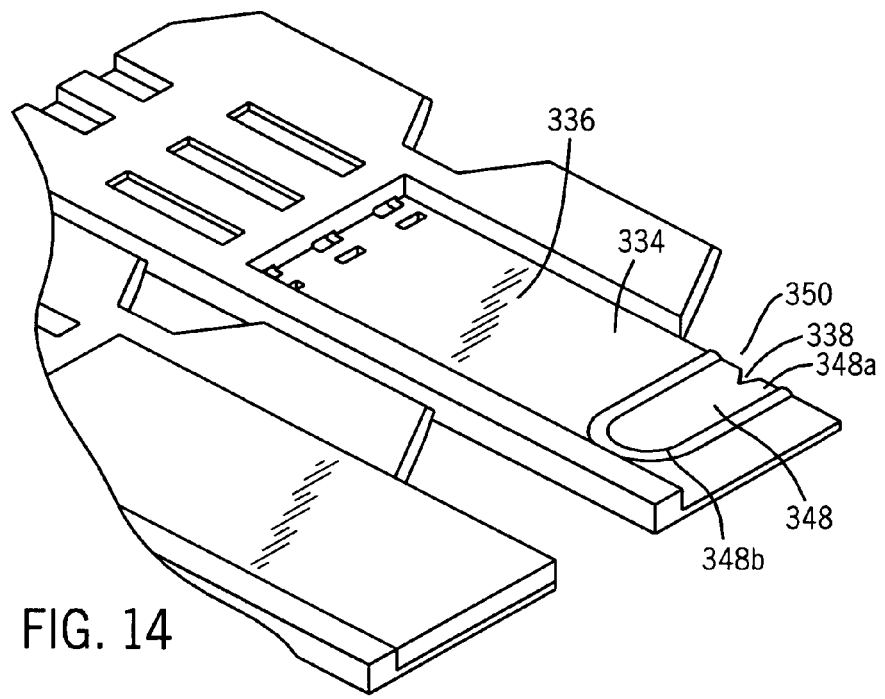
FIG. 14 is a perspective view, greatly enlarged, of an individual recess of the article of FIG. 12 and of FIG. 13.
Figure 15:
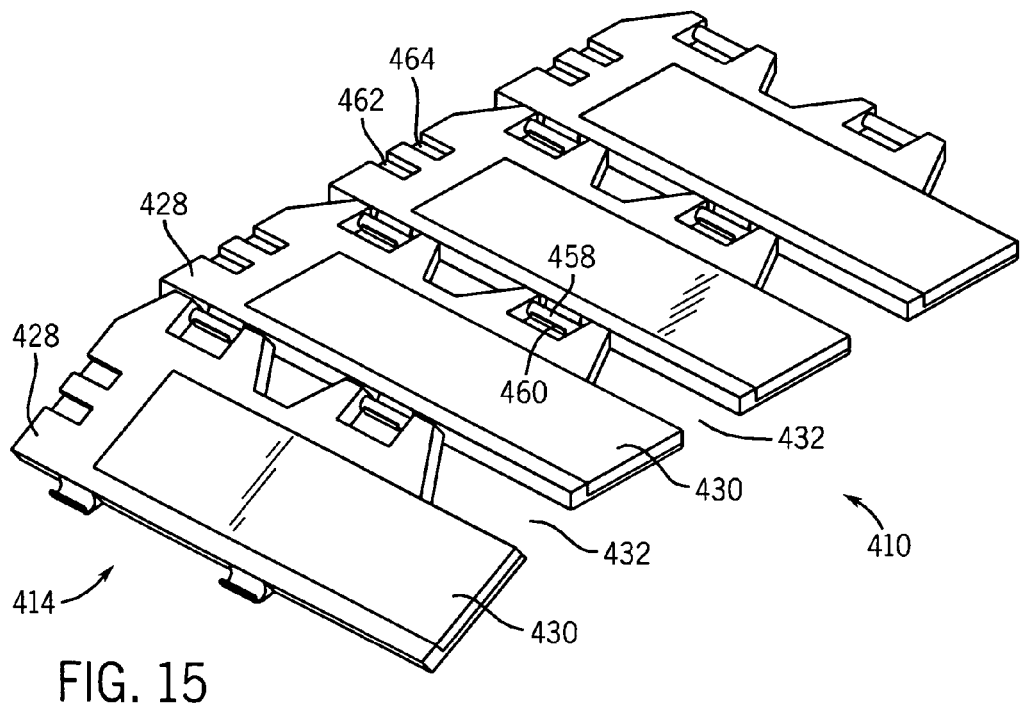
FIG. 15 is a perspective view of another embodiment of the article of this invention. In this figure, the article is shown as being unrolled. Also, in this figure, one major surface of each biosensor in the article is visible.

A fourth embodiment of the article of this invention is shown in FIGS. 12-14. In this embodiment, in which the biosensors can be packaged in a configuration that is somewhat similar to a roll or a cartridge, as in a film cartridge, the article 310 comprises a backing 314, which comprises a plurality of segments 328 that are arranged in a line. Each segment 328 is detachable from the segment 328 or segments 328 adjacent thereto. Each segment 328 has sufficient surface area to support a biosensor 330, e.g., a biosensor in the form of a test strip. In each segment 328, there is an aperture 332 adjacent to the test strip 330. The purpose of the aperture 332 is to allow passage of a lancing device for forming an opening in the skin and further for allowing biological fluid emerging from the opening in the skin to have access to the test strip 330. On one major surface 334 of the backing 314 are a plurality of recesses 336, one recess 336 per segment 328. These recesses 336 have the function of positioning and retaining the biosensors 330.

The biosensor 330 in each segment 328 has access to the aperture 332 through which biological fluid emerges from the patient. As shown in FIGS. 12-14, the aperture 332 is trapezoidal in shape and part of the aperture 332 is allocated to a given segment and part of the aperture 332 is allocated to the adjacent segment. However, the aperture 332 can be of a different shape and can be confined within a given segment. The aperture 332 of each segment 328 has a notch 338 for providing an area at which the biological sample can easily be drawn into the test strip 330. As in the embodiments shown in FIGS. 1-3 and 6-11, the notch 338 breaks the surface tension of the liquid and provides a larger surface area for application of a liquid sample. A layer of adhesive 340 can be used to adhere the test strip 330 to the backing 314.

Each of the recesses 336 has a first end 336a and a second end 336b and is of sufficient size and appropriate shape to accommodate a test strip 330. The depth of the recess 336 is approximately equal to or greater than the thickness of the test strip 330. The length of the recess 336 is approximately equal to or greater than the length of the test strip 330. The test strip will be described later.

As stated previously, the article 310 is in the form of a roll or cartridge, as in a film cartridge. The article 310 preferably contains a sufficient number of segments 328 for accommodating the desired number of test strips. The number of segments 328 in the article determines the length of the article. The overall depth of the backing 314 is not critical, but should be of sufficient length to ensure structural integrity. The depth must not be so great as to require the apparatus into which it is inserted to be excessively large. Further, the depth must not be so great that the article cannot be stored in the form of a roll. Typical dimensions of the backing 314 can range and from about 0.5 to about 5 mm in thickness. Each segment 328 should be of sufficient width to accommodate a single test strip 330. The backing 314 can be made of the same type of material that can be used to form the backing 114.

Each segment 328 has a channel 348 formed therein to allow for the flow of a liquid sample. As shown in FIG. 14, one end 348a of the channel 348 is adjacent to the aperture 332 to enable transfer of biological fluid from the subject to the channel 348. The other end 348b of the channel 348 terminates at a vent opening or a physical end of the channel or at a flow-terminating interface. The portion of the channel 348 between the two ends 348a and 348b can include a surfactant-coated mesh to aid the wicking of the sample info the reaction site. In other embodiments, the dimensions of the channel can be selected to allow the sample to be taken into the reaction site by capillary attraction.

At the end 348a of the channel 348 is a reaction site 350. The volume of the channel 348 is selected to contain the amount of sample needed to perform a test. The selection of the volume is based on the spacing of the electrodes of the electrode arrangement. The dimensions of the channel 348 are derived from the volume of liquid sample required. A typical volume for the channel 348 ranges from about 0.1 microliter to about 4 microliters, thereby calling for dimension of from about 0.5 mm×0.2 mm×0.1 mm to about 2 mm×1 mm×0.2 mm for a rectangularly-shaped channel.

The layer of adhesive 340 has an aperture 352 into which the biological fluid can pass into a channel 354 formed in the layer of adhesive 340. The channel 354 has a first end 354a and a second end 354b.

In one desirable variation of this embodiment, the segments 328 can be rendered more easily detachable by means of a rupturable link 356, or flexible connection, between adjacent segments 328. Adjacent segments can be separated by breaking the rupturable link, or flexible connection, by either tearing along a perforation or having a cutting device disconnect a given segment from an adjacent segment. In each segment there can be a slot 358 formed therein for facilitating the advancing of the segments 328 for moving the notch 338 closer to the sample of biological fluid emerging from the skin and through the aperture 332 so that the biological fluid can be readily taken up at the sample application zone of the test strip 330. A slot 360 adjacent to the slot 358 can be used for indexing of the segments 328 for in order to transport a used test strip 330 away from the lancing zone.

In FIG. 13 are shown electrical contact pads 362, which can be formed to increase the density of material of the electrical contacts and increase flexibility of the electrical contacts, e.g., with respect to orientation of electrical contacts within the meter. The electrical contacts 362 can be pre-formed and then placed in slots 364 to eliminate the need for printing the contacts on the biosensor. Pre-formed electrical contacts can be used in other embodiments at the discretion of the manufacturer.

A fifth embodiment of the article of this invention is shown in FIGS. 15-18. In this embodiment, which is also somewhat similar to a roll or a cartridge, as in a film cartridge, the article 410 comprises a backing 414, which comprises a plurality of segments 428 that are arranged in a line. Each segment 428 is detachable from the segment 428 or segments 428 adjacent thereto. Each segment 428 has sufficient surface area to support a biosensor 430, e.g., a biosensor in the form of a test strip. In each segment 428, there is an aperture 432 adjacent to the biosensor 430. The purpose of the aperture 432 is to allow passage of a lancing device for forming an opening in the skin and further for allowing biological fluid emerging from the opening in the skin to have access to the biosensor 430. On one major surface 434 of the backing 414 are a plurality of recesses 436, one recess 436 per segment 428. These recesses 436 have the function of positioning and retaining the test strips 430.

Figure 16:
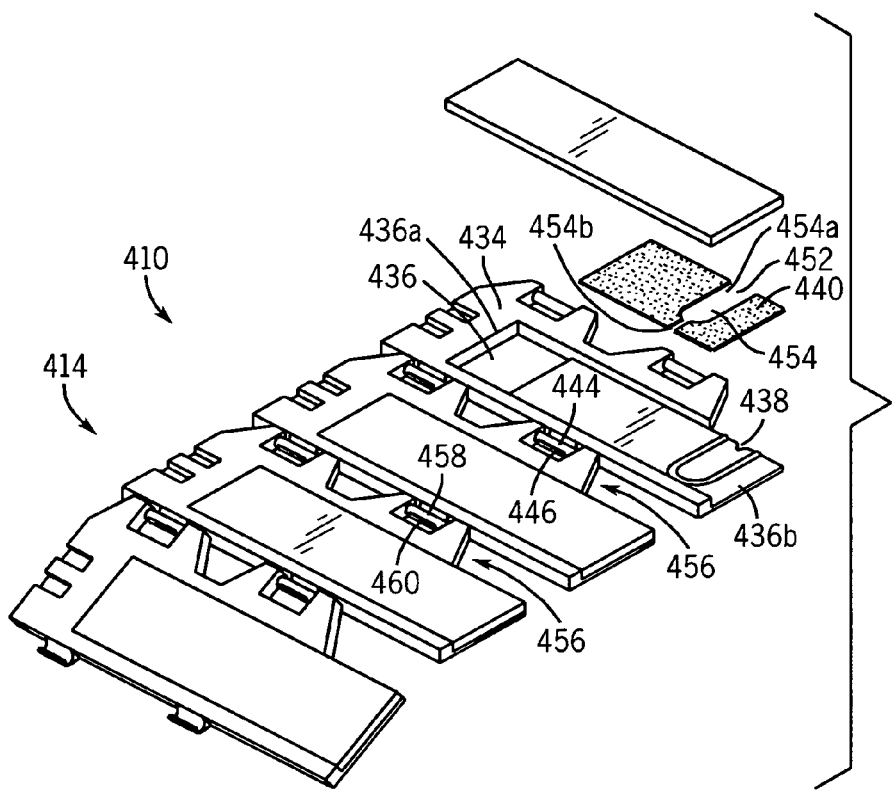
FIG. 16 is an exploded perspective view of the article of FIG. 15. Also, in this figure, a major surface of each biosensor in the article, the surface bearing the electrode arrangement, is not visible.
Figure 17:
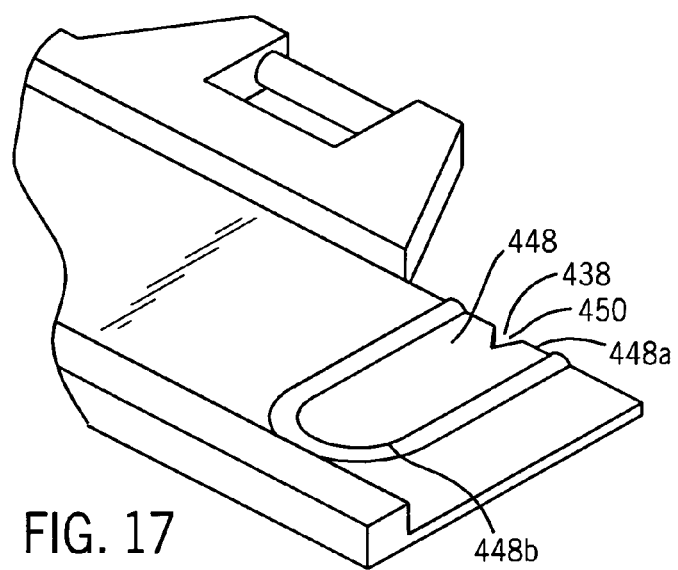
FIG. 17 is a perspective view, greatly enlarged, of an individual recess of the article of FIG. 15 and of FIG. 16.
Figure 18:
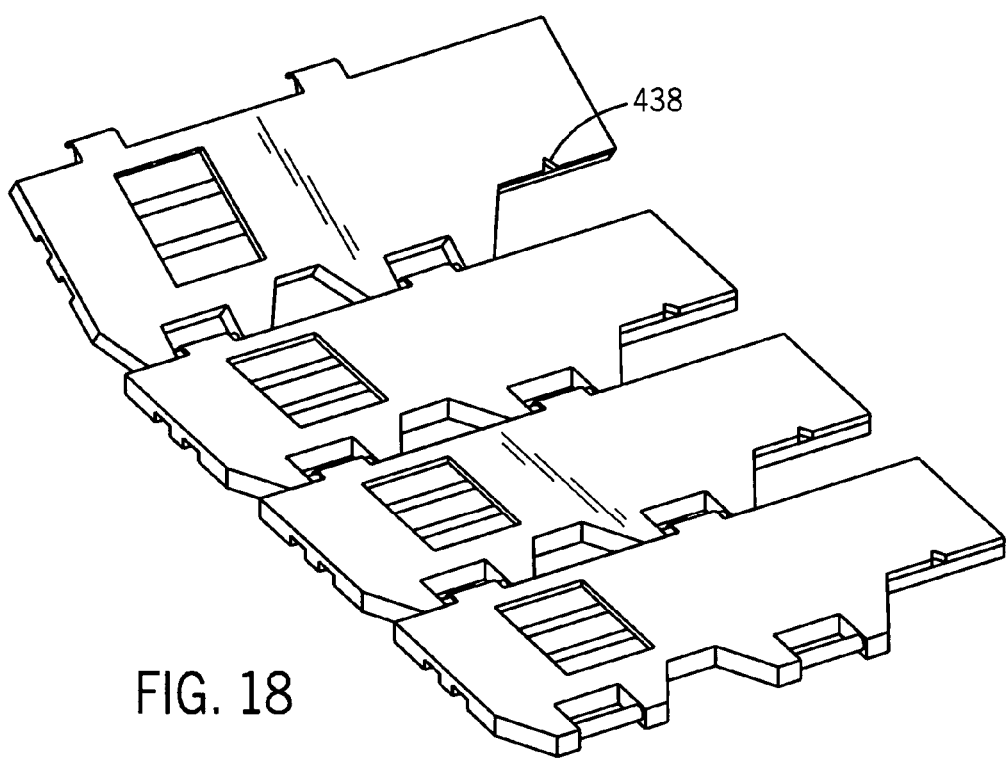
FIG. 18 is a second perspective view of the article of FIG. 15. In this figure, the article is shown as being unrolled. Also, in this figure, only a minor surface of each biosensor is visible.

The biosensor 430 in each segment 428 has access to the aperture 432 through which biological fluid emerges from the patient. As shown in FIGS. 16-18, the aperture 432 is trapezoidal in shape and part of the aperture 432 is allocated to a given segment and part of the aperture 432 is allocated to the adjacent segment. However, the aperture 432 can be of a different shape and can be confined within a given segment.

The aperture 432 of each segment 428 has a notch 438 for providing an area at which the biological sample can easily be drawn into the test strip 430. As in the embodiments shown in FIGS. 1-3, 6-14, the notch 438 breaks the surface tension of the liquid and provides a larger surface area for application of a liquid sample. A layer of adhesive 440 can be used to adhere the test strip 430 to the backing 414.

Each of the recesses 436 has a first end 436a and a second end 436b and is of sufficient size and appropriate shape to accommodate a test strip 430. The depth of the recess 436 is approximately equal to or greater than the thickness of the test strip 430. The length of the recess 436 is approximately equal to or greater than the length of the test strip 430. The test strip will be described later.

As stated previously, the article 410 is in the form of a roll or cartridge, as in a film cartridge. The article 410 preferably contains a sufficient number of segments 428 for accommodating the desired number of test strips. The number of segments 428 in the article determines the length of the article. The overall depth of the backing 414 is not critical, but should be of sufficient length to ensure structural integrity. The depth must not be so great as to require the apparatus into which it is inserted to be excessively large. Further, the depth must not be so great that the article cannot be stored in the form of a roll. Typical dimensions of the backing 414 can range and from about 0.5 to about 5 mm in thickness. Each segment 428 should be of sufficient width to accommodate a single test strip 430. The backing 414 can be made of the same type of material that can be used to form the backing 114.

Each segment 428 has a channel 448 formed therein to allow for the flow of a liquid sample. As shown in FIG. 17, one end 448a of the channel 448 is adjacent to the aperture 432 to enable transfer of biological fluid from the subject to the channel 448. The other end 448b of the channel 448 terminates at a vent opening or a physical end of the channel or at a flow-terminating interface. The portion of the channel 448 between the two ends 448a and 448b can include a surfactant-coated mesh to aid the wicking of the sample into the reaction site. In other embodiments, the dimensions of the channel can be selected to allow the sample to be taken into the reaction site by capillary attraction.

At the end 448a of the channel 448 is a reaction site 450. The volume of the channel 448 is selected to contain the amount of sample needed to perform a test. The selection of the volume is based on the spacing of the electrodes of the electrode arrangement. The dimensions of the channel 448 are derived from the volume of liquid sample required. A typical volume for the channel 448 ranges from about 0.1 microliter to about 4 microliters, thereby calling for dimension of from about 0.5 mm×0.2 mm×0.1 mm to about 2 mm×1 mm×0.2 mm for a rectangularly-shaped channel.

The layer of adhesive 440 has an aperture 452 into which the biological fluid can pass into a channel 454 formed in the layer of adhesive 440. The channel 454 has a first end 454a and a second end 454b.

In one desirable variation of this embodiment, the segments 428 can be rendered more easily detachable by means of a detachable link 456 between adjacent segments 428. The detachable link comprises a pin 458 and a holder for the pin 460. The holder 460 receives the pin 458. The detachable link can be broken by merely forcing the pin 458 out of the holder 460, thereby separating one segment from the adjacent segment. This type of detachable link may be preferable to the perforations and score lines and the other type of rupturable link on account of strength, flexibility, and the ability to pack more segments into the same volume of space. In each segment 428, there can be a slot 462 formed therein for facilitating the advancing of the segments 428 for moving the notch 438 closer to the sample of biological fluid emerging from the skin and through the aperture 432 so that the biological fluid can be readily taken up at the sample application zone of the test strip 430. A slot 464 adjacent to the slot 462 can be used for indexing of the segments 428 in order to transport a use test strip 430 away from the lancing zone.

Figure 19:
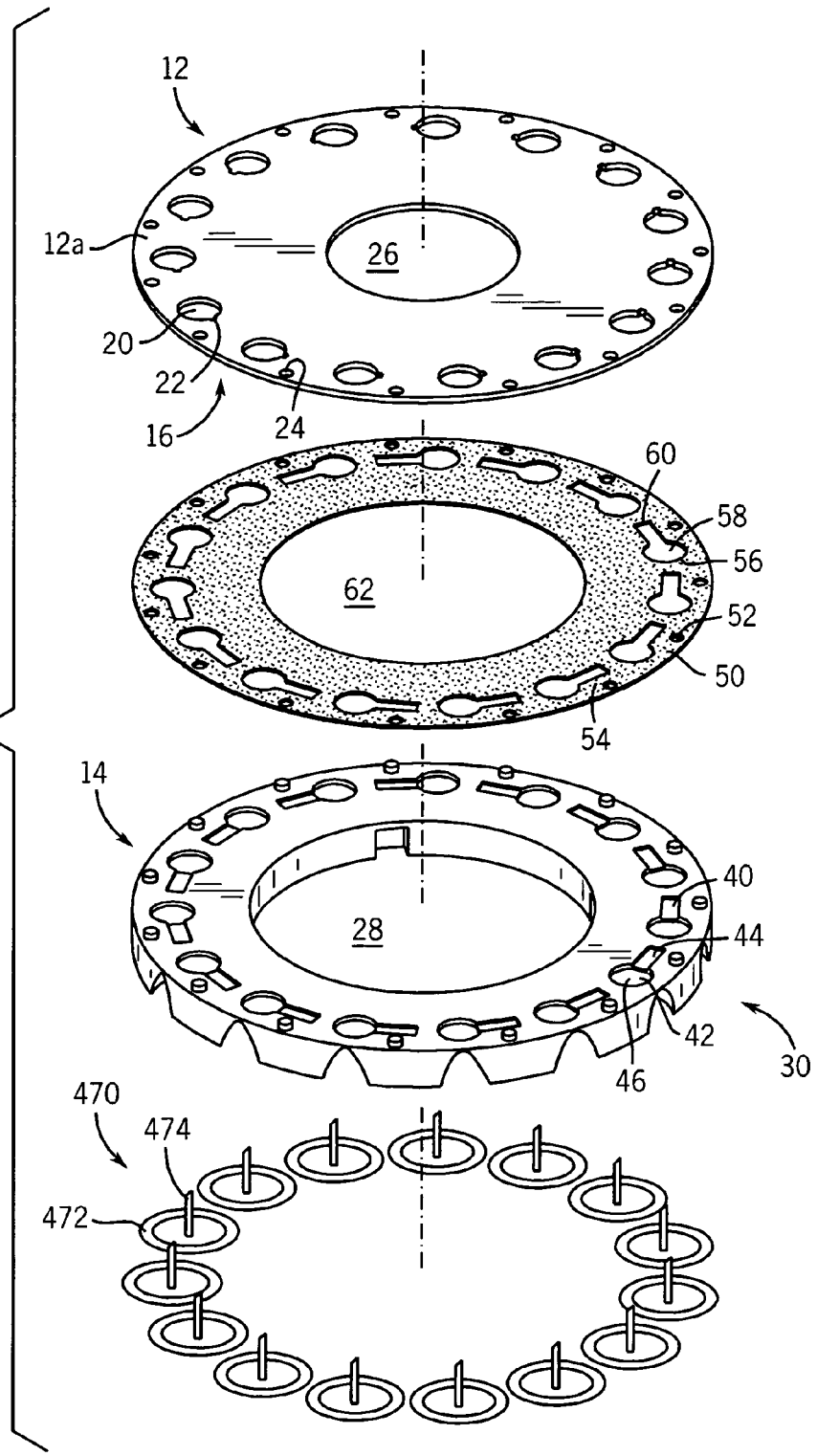
FIG. 19 is an exploded perspective view of another embodiment of the article of this invention, wherein a plurality of single-use lancet attachments is utilized. The article is similar to the article shown in FIGS. 1-3.
Figure 20:
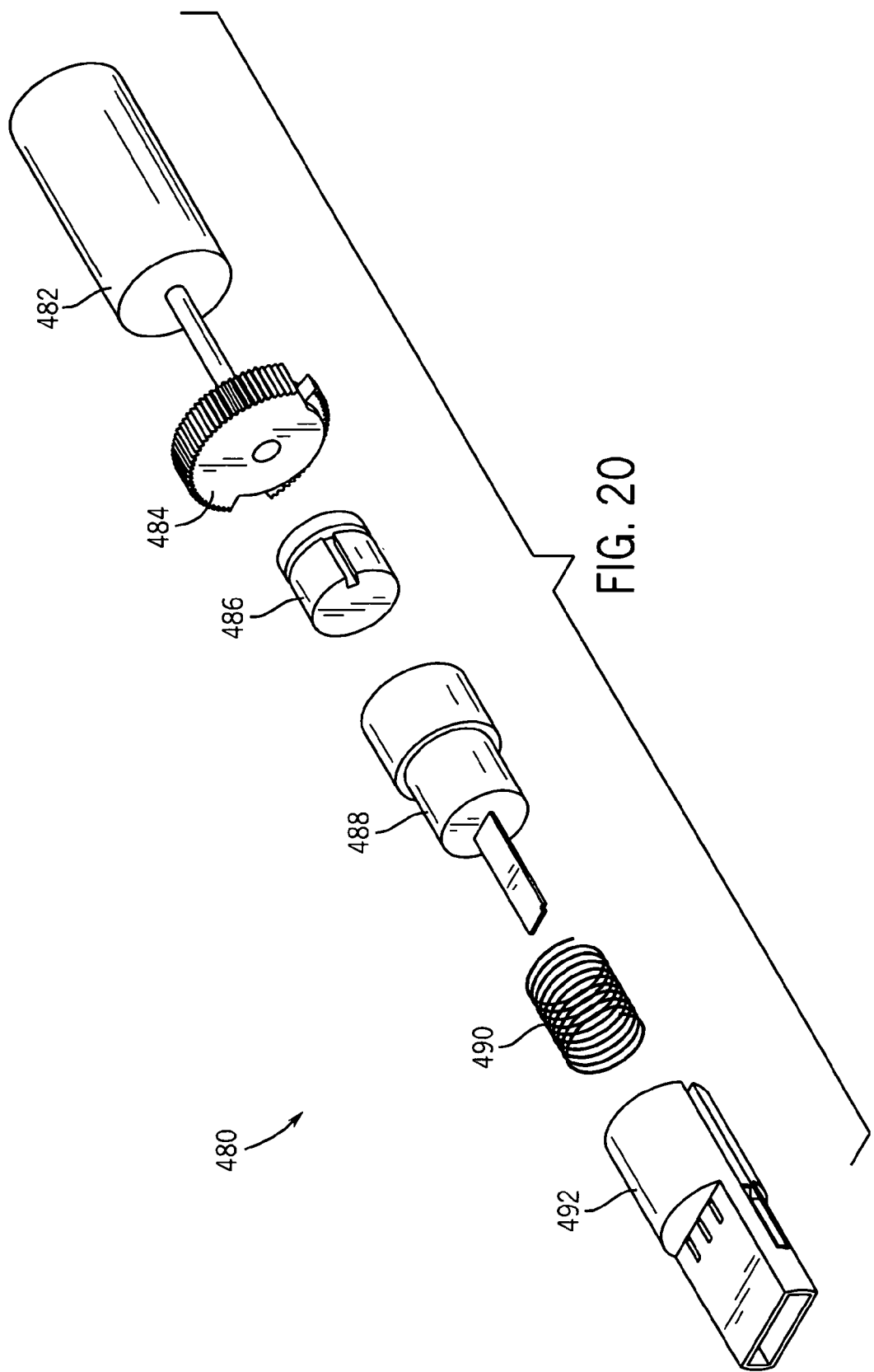
FIG. 20 is an exploded perspective view of a percussion device that can be adapted to activate the lancet attachments shown in FIG. 19.

A sixth embodiment of the article of this invention is shown in FIG. 19. In this embodiment, a single-use lancet is employed for each biosensor. In this embodiment, which is shown as a variation of the embodiment shown in FIGS. 1-3 or of the embodiment shown in FIGS. 6-8, a plurality of lancet attachments 470 are fitted into the backing 14, one lancet attachment 470 per sector 30. The lancet attachment 470 includes a head 472 and a blade 474. The blades 474 in the lancet attachment 470 can be activated to form an opening in the skin of a patient by means of a percussion device, an example of which is shown in FIG. 20. The percussion device 480 comprises a motor 482, a depth adjustment mechanism 484, a cam 486, a hammer 488, a return spring 490, and a port 492. When a switch (not shown) is activated to begin a test involving a biosensor, the motor 482 is activated and drives the cam 486. The rotational movement of the cam 486 is translated into linear motion of the hammer 488. The hammer 488 advances and strikes the head 472 of the lancet attachment 470. The blade 474 of the lancet attachment 470 is then advanced along its path of travel through the skin of the patient or subject. The blade 474 of the lancet attachment 470 is then retracted. Retraction of the blade 474 of the lancet attachment 470 can be carried out in several ways. One simple way involves the use of a head 472 that is made of a resilient material, e.g., steel, plastic, rubber, and is the shape of a dome. The shape of the dome need not be hemispherical (i.e., arc of the dome being 180°). The arc of the dome can be at an angle of less than 180°. The resilient material causes the dome-shaped head 472 to be resiliently biased, so that when the blade 474 is in the retracted position, the edge of the dome-shaped head 472 is approximately at the same level as the tip of the blade 474. When the hammer 488 strikes the dome-shaped head 472, the resiliency of the material of the dome-shaped head causes the dome-shaped head to flatten to a sufficient extent to cause the blade 474 to be forced into the skin, thereby forming an opening in the skin. When the return spring 490 moves the hammer 488 away from the dome-shaped head 472 of the lancet attachment 470, the resilient biasing of the dome-shaped head 472 causes the head to reform into the shape of the dome and to revert to its normal position, whereby the blade 474 is retracted and again the tip of the blade 474 will be approximately at the same level as the edge of the dome-shaped head 472. The sample emerges from the opening formed in the skin by the blade 474 and is transferred directly to the proper position on the biosensor. The depth adjustment mechanism 484 is set by the user to specify the length of travel of the hammer 488. The port 492 serves as a guide for the hammer 488.

Turning now to a discussion of the biosensors, biosensors of the electrochemical type can be printed onto a thin, flat plate as in FIGS. 1-3 or can be pre-manufactured test strips as in FIGS. 6-18. The choice of using a printed biosensor or a pre-manufactured test strip is in the discretion of the manufacturer.

The same, or similar, electrode arrangement can be used for each embodiment, or a different electrode arrangement can be used for each embodiment. For ease of manufacture, it is preferred that only one electrode arrangement be used in each embodiment.

Figure 21:
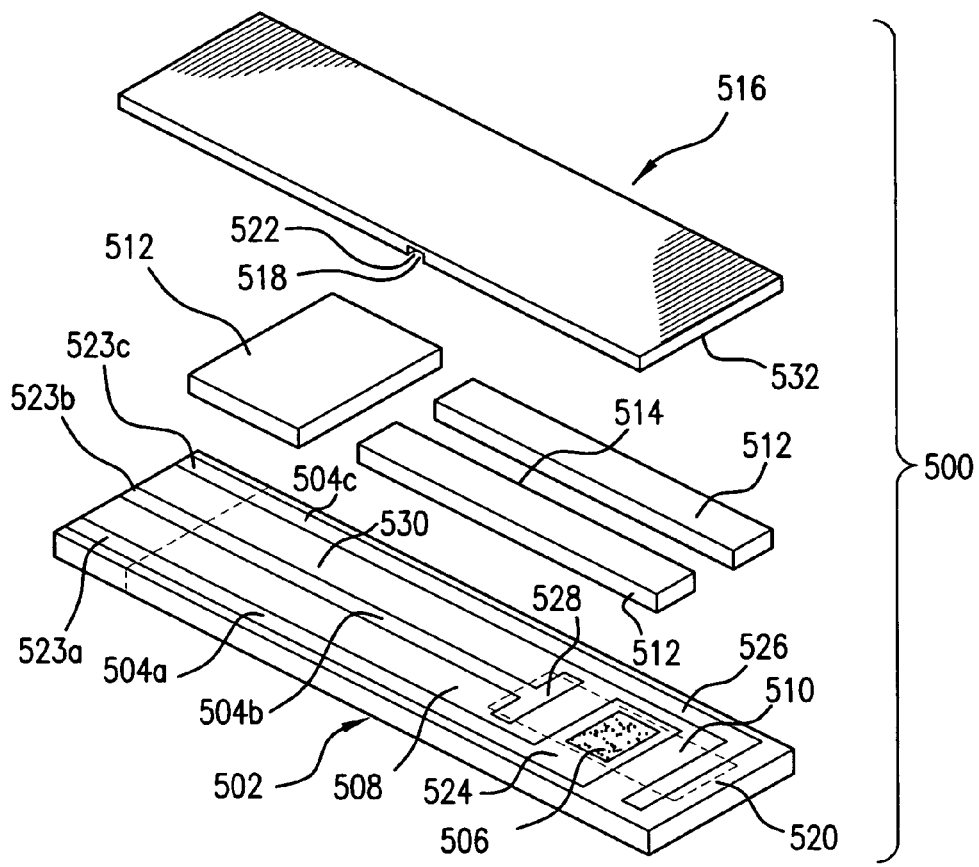
FIG. 21 is a perspective view of a biosensor suitable for use in the articles of FIGS. 6-18.
Figure 22:
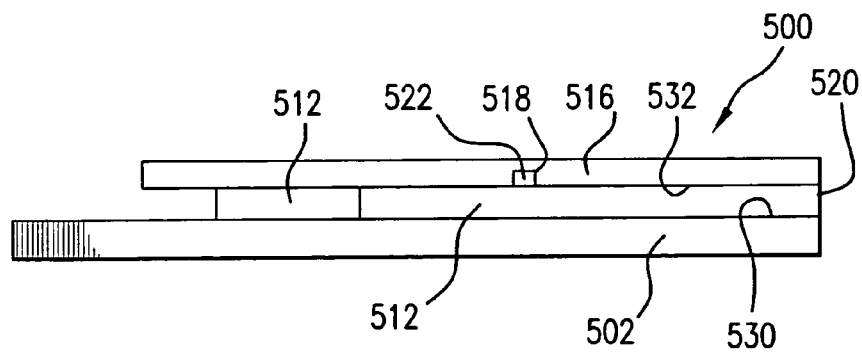
FIG. 22 is a side view in elevation of the biosensor of FIG. 21.

Referring now to FIGS. 21 and 22, a biosensor 500, which is in the form of a test strip, comprises a base layer 502, conductive tracks 504a, 504b, and 504c for electrochemical use, a reaction site 506, an insulating layer 508 to delineate a specified sensor area 510, a spacer layer 512 to specify the width and depth of a flow channel 514, a cover layer 516 to enclose the flow channel 514. The sample is caused to flow in the flow channel 514 by means of capillary attraction. A flow-terminating interface is designated by the reference numeral 518. A sample application zone is designated by the reference numeral 520. Such a biosensor is shown in detail in U.S. application Ser. No. 10/266,548, filed Oct. 8, 2002, which is now U.S. Application Publication No. 2004-0067166-A1, published Apr. 8, 2004, incorporated herein by reference.

Sensor response is compromised if the sample flows during the analysis; thus, termination of the flow of the sample is extremely desirable. At least one opening 522 is formed in the sensor strip 500 in communication with the flow channel 514 to bleed air to reduce the pressure that resists uptake of the sample. This pressure prevents the sample from traversing the flow channel 514.

The base layer 502 is preferably made of an inert polymeric material. Representative materials that can be used to form the base layer 502 include, but are not limited to, poly(vinyl chloride), polycarbonate, and polyester. The dimensions of the base layer 502 are not critical, but a typical base layer 502 has a length of from about 20 mm to about 40 mm, a width of from about 3 mm to about 10 mm, and a thickness of from about 0.5 mm to about 1 mm.

The conductive tracks 504a, 504b, and 504c are made of an electrically conductive material. Representative materials that can be used to form the electrically conductive tracks 504a, 504b, and 504c include, but are not limited to, carbon, platinum, palladium, gold, and a mixture of silver and silver chloride. The tracks 504a, 504b, and 504c determine the positions of electrical contacts 523a, 523b, and 523c, respectively, and the electrodes, which will be described later. The third track can be omitted in the absence of a third electrode. The electrical contacts are insertable into an appropriate measurement device (not shown).

The reaction site 506 comprises an arrangement of electrodes, and, optionally, one or more layers of reagents. The electrode arrangement of the sensor strip preferably includes either two or three electrodes. In a two-electrode system (not shown), a working electrode and dual-purpose reference/counter electrode define the electrode arrangement. A third electrode (trigger electrode) can be optionally added to indicate that the reaction site 506 is filled. The trigger electrode prevents the assay from beginning until an adequate quantity of sample has filled the reaction site 506. A two-electrode system is described more completely in U.S. Pat. No. 5,509,410, incorporated herein by reference. The reference electrode can be positioned so as to act as a trigger electrode to initiate the assay sequence in the absence of the third electrode.

In a three-electrode system, which is illustrated in FIGS. 21 and 22, a working electrode 524, a reference electrode 526, and a counter electrode 528 define the electrode arrangement. The function of the working electrode 524 is to measure the reaction that takes place in the reaction site 506, e.g., the reaction of glucose with glucose oxidase or glucose dehydrogenase. The function of the reference electrode 526 is to maintain a desired potential at the working electrode. The function of the counter electrode 528 is to provide the necessary current flow at the working electrode 524. In this system the counter electrode 528 can have the secondary function of a trigger electrode, that is, prevents the assay from beginning until an adequate quantity of sample has filled the reaction site 506.

The reaction that takes place at the working electrode 524 is the reaction that is required to be measured and controlled, e.g., the reaction of glucose with glucose oxidase or with glucose dehydrogenase. The functions of the reference electrode 526 and the counter electrode 528 are to ensure that the working electrode 524 actually experiences the desired conditions, i.e. the correct potential. The potential difference between the working electrode 524 and the reference electrode 526 is assumed to be the same as the desired potential at the working electrode 524. In an ideal reference electrode, no current passes through the reference electrode, and the reference electrode maintains a steady potential; in the case of a dual-purpose reference/counter electrode, current does pass through the dual-purpose reference/counter electrode, and thus, the dual-purpose reference/counter electrode does not maintain a steady potential. At low currents, the potential shift is small enough such that the response at the working electrode is not significantly affected, and hence the dual-purpose reference/counter electrode is designated a pseudo-reference electrode. The dual-purpose reference/counter electrode still carries out its counter electrode function; however, in the case of the dual-purpose reference/counter electrode, the potential that is applied between the dual-purpose reference/counter electrode and the working electrode cannot be altered to compensate for changes in potential at the working electrode.

The electrodes 524, 526, and 528 are made of an electrically conductive material. Representative materials that can be used to form the electrodes 524, 526, and 528 include, but are not limited to, carbon, platinum, palladium, and gold. The reference electrode 526 can optionally contain a layer comprising a mixture of silver and silver chloride. The dimensions of the electrodes 524, 526, and 528 are not critical, but a typical working electrode has an area of from about 0.5 mm$^2$ to about 5 mm$^2$, a typical reference electrode has an area of from about 0.2 mm$^2$ to about 2 mm$^2$, and a typical counter electrode has an area of from about 0.2 mm$^2$ to about 2 mm$^2$.

The working electrode 524 comprises a layer of conductive material containing a working area. The working area can include an ink (referred to a working ink), which is deposited on the layer of conductive material of the working area. The working ink comprises a reagent system that is sensitive to the analyte of interest.

The working area is formed from a working ink that includes a reagent suitable for the subject test. The reagent may include a mixture of an enzyme (e.g., glucose dehydrogenase or glucose oxidase for a glucose assay), a redox mediator (such as an organic compound, e.g., a phenanthroline quinone, an organometallic compound, e.g., ferrocene or a ferrocene derivative, a coordination complex, e.g., ferricyanide), and a conductive filler material (e.g., carbon) or non-conductive filler material (e.g., silica). Alternatively, instead of an enzyme, the working area can contain a substrate that is catalytically reactive with an enzyme to be measured. The respective printing inks are applied to the electrode 524, and, optionally, electrode 526 or electrode 528, or both, as discrete areas of fixed length. The printing inks can applied by means of screen-printing. The printing inks can further include a polysaccharide (e.g., a guar gum, an alginate, cellulose or a cellulosic derivative, e.g., hydroxyethyl cellulose), a hydrolyzed gelatin, an enzyme stabilizer (e.g., glutamate or trehalose), a film-forming polymer (e.g., a polyvinyl alcohol), a conductive filler (e.g., carbon) or non-conductive filler (e.g., silica), a defoaming agent, a buffer, or a combination of the foregoing.

The electrodes cannot be spaced so far apart that the working electrode 524, the reference electrode 526, and the counter electrode 528 (or the dual-purpose reference/counter electrode and the working electrode in an alternative embodiment) cannot be covered by the sample. It is preferred that the length of the path to be traversed by the sample (i.e., the sample path) be kept as short as possible in order to minimize the volume of sample required. The maximum length of the sample path can be as great as the length of the sensor strip. However, the corresponding increase in resistance of the sample limits the length of the sample path to a distance that allows the necessary response current to be generated. The solution resistance is also influenced by the distance from the edge of the area of the reference electrode 526 to the edge of the working area of the working electrode 524 (or by the distance from the dual-purpose reference/counter electrode to the edge of the working area of the working electrode in an alternative embodiment). Reducing the distance between the reference electrode 526 and the working electrode 524 (or the dual-purpose reference/counter electrode from the working electrode in an alternative embodiment) decreases the solution resistance. Positioning the electrodes in a spaced-apart manner has the advantage of preventing completion of a circuit (and thus preventing detection of a response current) before the working electrode has been completely covered by sample.

The elongated portions of the conductive tracks 504a, 504b, and 504c can optionally be overlaid with a track of conductive material, preferably made of a mixture comprising silver particles and silver chloride particles. This optional overlying track results in lower resistance, and consequently, higher conductivity. Optionally, a layer of a hydrophobic electrically insulating material 508 further overlies the tracks 504a, 504b, and 504c. The layer of hydrophobic electrically insulating material 508 does not cover the positions of the reference electrode 526, the working electrode 524, the counter electrode 528, and the electrical contacts. In the embodiment employing the dual-purpose reference/counter electrode (in an alternative embodiment), the layer of hydrophobic electrically insulating material does not cover the positions of the dual-purpose reference/counter electrode, the working electrode, any third electrode, and the electrical contacts. This layer of hydrophobic electrically insulating material 508 serves to prevent short circuits. Because this insulating material is hydrophobic, it can cause the sample to be restricted to the exposed electrodes. A preferred insulating material is commercially available as "POLYPLAST" (Sericol Ltd., Broadstairs, Kent, UK).

The reaction site 506 is not limited to reaction sites appropriate to electrochemical sensors. In a photometric sensor (not shown), the reaction site can comprise a reagent system that changes its optical properties (e.g., absorbance, reflectance) as a function of the presence of or the amount of an analyte. A photometric sensor is similar to the sensor shown in FIGS. 1, 2, 3, and 4, with the exception that the electrodes and tracks are removed, and, at the reaction site, at least a portion of the flow channel comprises a light transmissive material so that a source of light can transmit light through the light transmissive material to provide a signal related to the presence or the amount of an analyte in the sample, e.g., absorbance or reflectance. This optical signal can be detected and measured. In conjunction with the light transmissive material, at least one reagent for a specified assay can be located at or transported to the reaction site. In still another type of sensor (not shown), the reaction site can comprise an ion-selective electrode.

The spacer layer 512 comprises a material of substantially uniform thickness that can bond to the first major surface 530 of the base layer 502 and to the first major surface 532 of the cover layer 516.

In certain embodiments, the base layer 502 is not required. For example, in the embodiments shown in FIGS. 1-3, no base layer is required—the thin, flat plate 12 itself performs the functions of the base layer 502.

Capillary attraction is very desirable as the fluid transfer mechanism for the biological fluid. The analyte meter can be designed to use the same indexing mechanism to move the entrance of a capillary channel of a given test strip to the lancing site after the lancing step to collect a sample of biological fluid, e.g., blood.

One of the key benefits of this invention is the multiple-biosensor article for an apparatus that integrates lancing the skin of a patient, collecting biological fluid from the patient, e.g., blood, and measuring the concentration of an analyte in the biological fluid of the patient. The invention eliminates the manual handling of individual test strips, the manual lancing of the skin of the patient, and the manual collecting of biological fluid from the patient.

Because there is no need to handle each test strip individually, the physical size of each test strip can be greatly reduced. As a consequence, the number of biosensors that can be placed in a given area of a multiple-biosensor article can be increased.

The multiple-biosensor article can be made in a number of ways, some of which will be described. In the embodiment shown in FIGS. 1-3, a plurality of biosensors are printed on a thin, flat, circular plate such that the electrically conductive tracks are aligned along the radius of the plate. The electrodes are located near the periphery of the thin, flat plate and the electrical contacts are located toward the center of the thin, flat, circular plate. The plate has apertures adjacent to the electrodes in order to allow the skin to be pierced by the lancing device that moves perpendicular to and through the major surfaces of the plate. The same effect can be achieved by a cutting an area of the plate that is adjacent to the electrodes in order to provide unrestricted area for the skin to be pierced.

The thin, flat plate 12 is then attached to the backing 14. Attachment can be achieved, for example, by using an adhesive layer or by an interlocking mechanism, e.g., a press-fit ring. As shown in FIGS. 1-3, the backing 14 has apertures 38 in the recessed portions 32 that will be aligned with the apertures 20 on the plate 12. The plate 12, the layer of adhesive 50, and the backing 14 cooperate to form a plurality of capillary chambers. Each of these capillary chambers will be associated with an electrode arrangement, and the combination will be sufficient for creating a biosensor suitable for performing an assay.

The backing 14 can be formed from a polymeric material by means of an injection molding technique. Injection molding is a common technique used to create plastic components. The backing 14 can be molded in single form or be molded with a carrier to assist in manufacturing. A carrier would allow for the parts to be stored and transported on a reel for subsequent feeding into a continuous assembly step at a later time. It is preferred, but not required, that the backing 14 have features to enable alignment of the plate 12 with the backing 14.

As stated previously, the electrode arrangements can be prepared by screen printing inks onto a major surface of the plate 12.

The stages of ink deposition and their variations are well known to those of ordinary skill in the art. Descriptions of printing can be found, for example, in U.S. Pat. No. 5,509,410, incorporated herein by reference.

A layer of mesh and a layer of tape would not be required. These two components would be replaced by the backing (i.e., at least one surface of the backing would duplicate the function of the mesh and tape). A suitable material for adhering the backing to the plate is a double-stick adhesive tape. Some benefits of the use of tape would be ease of handling and control of the depth and perimeter of the channel. Once the plate and the backing are combined, the product is substantially ready for use.

In the embodiment shown in FIGS. 1-3, the backing can be prepared by injection molding. In the embodiment shown in FIGS. 6-8, the backing can be prepared by injection molding and the biosensors can be inserted into the recesses by machinery. In the embodiments shown in FIGS. 9-14, the backing can be prepared by injection molding and the biosensors can be inserted into the recesses by machinery. In the embodiment shown in FIGS. 15-18, the segments can be prepared by injection molding, assembled to form the backing, and the biosensors can be inserted into the recesses by machinery. Biosensors that are not printed onto the plate 12 or the backing 14 can be manufactured in a conventional manner and inserted into the appropriate recesses of the article by machinery.

In each embodiment described herein, there is an opening in or near each sector or each segment through which the lancing device can pass on the way to lancing the skin. The lancing device is preferably oriented perpendicular to the surface of the plate 12 or to the surface of the segment of a roll. The multiple-biosensor article can be used with all types of mechanical and laser lancing devices. The various test strips are used in sequence, not simultaneously.

Figure 4:
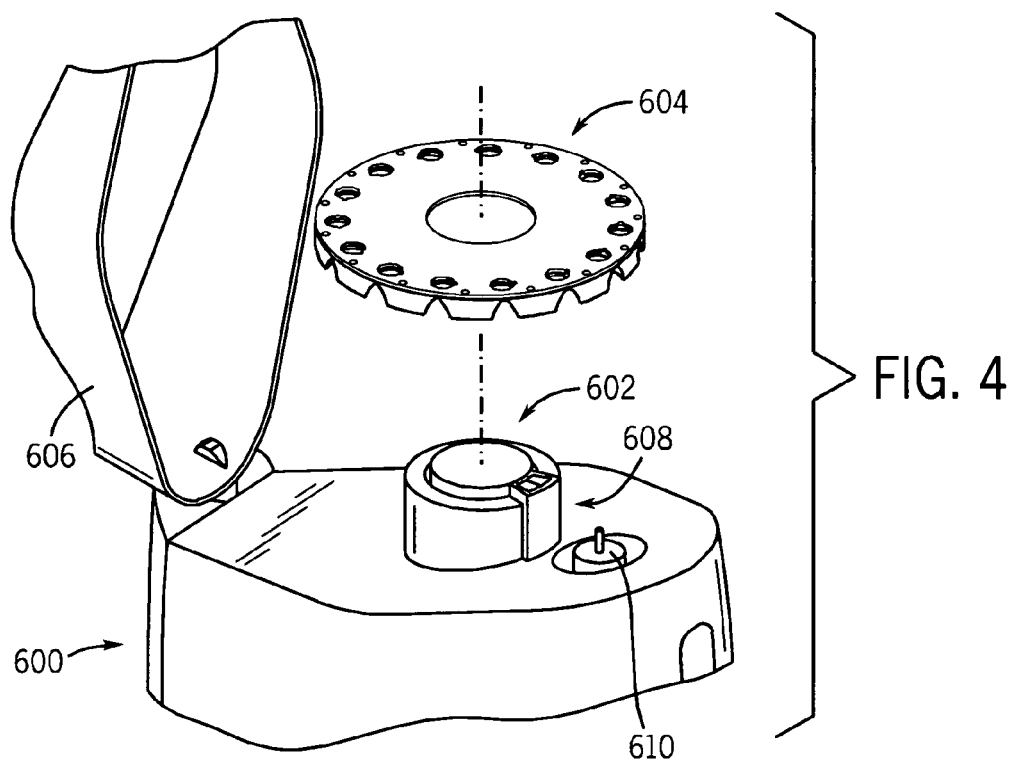
FIG. 4 is a perspective view of the article of this invention showing how the article of FIG. 1 is placed in an analyte meter.
Figure 5:
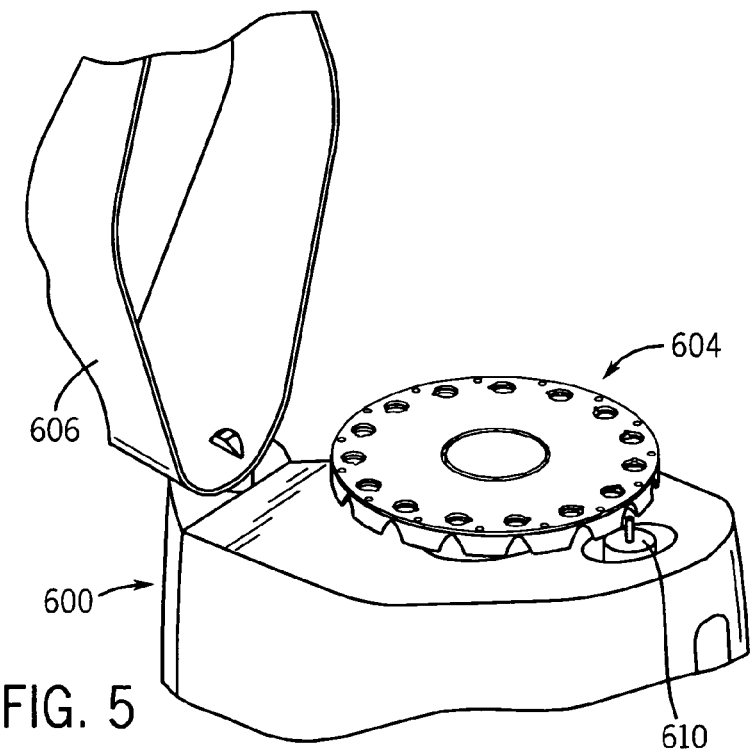
FIG. 5 is a perspective view of the article of this invention showing the article of FIG. 1 after being placed in an analyte meter.

The multiple-biosensor article should be of a size to fit within an analyte meter. As shown in FIGS. 4 and 5, an analyte meter 600 comprises a chamber 602 for accommodating the article 604 of this invention. The chamber 602 contains the mechanism(s) (not shown) required to allow positioning of the article for testing, pausing, and for removal after testing. This positioning or indexing function can be carried out automatically, semi-automatically, or manually.

The multiple-biosensor article can be loaded into the analyte meter 600 by inserting the article 604 into a slot located on or in the analyte meter, which slot communicates with the aforementioned chamber (not shown). The slot provides a path for the article to follow so that it can be moved into a stand-by or a test position. Another method of loading the article into analyte meter 600 would involve opening a door or cover 606 on or in the analyte meter 600 and inserting the article 604 into the area provided. In the embodiment shown in FIGS. 4 and 5, the article is placed on a rotatable platform 608, which is designed to rotate in order to position a given biosensor in the appropriate area for the lancing of the skin of a patient and the collection of biological fluid from the opening in the skin of the patient.

Once loaded in the analyte meter 600, the multiple-biosensor article 604 can be advanced or indexed or both by either rotating or translating the article automatically, semi-automatically, or manually. Advancing or indexing or both can be carried out by such mechanisms as motor(s), gear(s), pulley(s), belt(s), solenoid(s), nano-muscle(s), and the like (not shown).

After the lancing step, the multiple-biosensor article can be indexed slightly to cover the lancing site with the sample pick-up area of a biosensor to fill the reaction site of the biosensor.

After a test is completed, the flat, circular embodiments of this invention (e.g., FIGS. 1-3) may be advanced or indexed by rotation, automatically, semi-automatically, or manually, toward a storage area within the analyte meter. Used biosensors in the flat, circular embodiment may have to remain within the analyte meter until all of the biosensors are consumed. After the biosensors of the flat, circular embodiments have been used, they can be removed simply by lifting the article 604 off the rotatable platform 608. For the linear embodiments (e.g., FIGS. 6-18), only the segment used for the most recent test need be advanced or translated to an area that would allow for its removal either automatically or manually.

In order to use the device of this invention in an effective manner, the analyte meter has a drive mechanism to advance a given biosensor when it is required for a test. In the embodiments where the multiple-biosensor article is in the shape of a disk, the drive mechanism should be capable of rotating the disk about its axis. Mechanisms for rotating disk-shaped objects are well-known in the art. Representative examples of mechanisms capable of rotating disk-shaped objects include, but are not limited to, motors, gears, solenoids, nano-muscles, belts, linkages, pulleys, etc. In the embodiments where the multiple-biosensor article is in the configuration of a roll (or fan-fold, or round track, or L-shape), the drive mechanism should be capable of advancing the segments linearly to the area where the biological sample is to be collected. Representative examples of mechanisms capable of advancing segments of a roll linearly include, but are not limited to, motors, gears, solenoids, nano-muscles, belts, linkages, pulleys, etc.

The article of this invention can include calibration to minimize the number of steps required to perform a test for determining the concentration of an analyte. Calibration techniques suitable for use herein include, but are not limited to, a memory device (integrated circuit), resistive, or mechanical feature.

Various types of indicators for Identifying particular assays for particular analytes (ketone, glucose) can be employed with the article of this invention.

The adhesive suitable for use herein can be of the two-sided tape variety. Alternatively, in place of a two-sided tape, a liquid adhesive can be used. Such a liquid adhesive could be applied via screen printing or pad printing.

Various modifications and alterations of this invention will become apparent to those skilled in the art without departing from the scope and spirit of this invention, and it should be understood that this invention is not to be unduly limited to the illustrative embodiments set forth herein.

It should also be noted that various modifications and alterations shown in certain embodiments of the invention, illustrated herein, can be used in other embodiments. Such modifications and alterations include, but are not limited to, the means for separating adjacent segments of a roll or a cartridge, or the like, the means for applying the electrical contacts of the biosensors, and the types of biosensors and electrode arrangements for a given embodiment, e.g., the use of biosensors having electrode arrangements that are printed directly onto a sector of a thin, flat plate or a segment of a roll or a cartridge, or the like, the use of pre-formed test strips that are subsequently applied to a recess in a segment of a roll or a recess in a backing.

What is claimed is:

1. An article for providing a plurality of test strips, said article comprising:
   (a) a thin, flat plate comprising 1) a sample receiving side and 2) a backing-facing side that is opposite the sample receiving side;
   wherein said thin, flat plate has a plurality of sectors, each of said sectors comprising: an electrode arrangement applied thereto on the backing-facing side, and a first aperture for receiving a sample, wherein the electrode arrangement is adjacent the first aperture;
   (b) a backing comprising 1) a lancet-receiving side and 2) a plate-facing side that is opposite the lancet-receiving side, wherein the plate-facing side faces the backing-facing side of the thin, flat plate;
   wherein the backing has a plurality of sectors, each of said sectors having a recessed portion on the lancet-receiving side of the backing, the recessed portion comprising a wall portion and a base portion, and wherein the base portion includes a second aperture therethrough, wherein the wall portion is arranged and configured to guide a lancing device through the recessed portion and second aperture in from the lancet-receiving side and out the plate-facing side of the backing;
   wherein the plate-facing side of the backing includes a flow channel extending from the second aperture along a major surface of the plate-facing side of the backing, and wherein the flow channel is in register with the second aperture and said electrode arrangement;
   wherein said major surface of said plate-facing side of the backing is in facing orientation to the backing-facing side of said thin, flat plate such that the flow channel is on the plate-facing side of the backing and in facing arrangement with the electrode arrangement;
   wherein said first aperture is in facing arrangement with said second aperture, said first aperture is in register with said second aperture in said base portion of said backing, wherein the electrode arrangement is disposed on the thin, flat plate adjacent to the first and second apertures;
   wherein said lancing device passes first through the recessed portion of the lancet-receiving side of said backing and then through said second and first apertures out to the sample receiving side of the thin, flat plate.

2. The article of claim 1, wherein each of said first apertures in said thin, flat plate has a notch located on the periphery thereof.

3. The article of claim 1, wherein one major surface of said thin, flat plate is adhered to said major surface of said backing comprising said second aperture.

4. The article of claim 3, wherein a layer of adhesive adheres said one major surface of said thin, flat plate to said major surface of said backing, said layer of adhesive comprising a plurality of channels for the transport of biological fluid from the skin of a patient to said electrode arrangements.

5. The article of claim 1, wherein said thin, flat plate has a central opening and said backing has a central opening.

6. The article of claim 1, wherein the major surfaces of said thin, flat plate and said backing are circular in shape.

7. The article of claim 6, wherein said article is advanced by rotating said article.

8. The article of claim 1, further including a plurality of alignment posts for ensuring that said first aperture in said thin, flat plate is in register with said second aperture in said recessed portion in said backing.

9. The article of claim 1, wherein said backing is attached to said thin, flat plate by means of press-fitting.

10. The article of claim 1, wherein said backing is attached to said thin, flat plate by means of a weld.

11. The article of claim 1, wherein each electrode arrangement comprises a working electrode and a second electrode.

12. The article of claim 11, wherein the second electrode is a counter electrode and said electrode arrangement further comprises a reference electrode.

13. The article of claim 12, wherein said counter electrode functions as a trigger electrode.

14. The article of claim 1, wherein said first and second apertures are circular in shape.

15. The article of claim 1, wherein said thin, flat plate and said backing are made of polymeric material.

16. The article of claim 1, wherein said flow channel includes a mesh.

17. The article of claim 1, wherein said flow channel has a volume ranging from 0.1 to 4 µL.

18. The article of claim 1, further comprising a plurality of lancets.

19. The article of claim 18, wherein said plurality of lancets comprises a head and a blade.

20. The article of claim 1, wherein said electrode arrangement comprises a working electrode and a dual-purpose reference/counter electrode.

21. The article of claim 1, wherein said article is used for a glucose assay.

* * * * *